United States Patent
Lunner et al.

(10) Patent No.: US 10,820,121 B2
(45) Date of Patent: Oct. 27, 2020

(54) HEARING DEVICE OR SYSTEM ADAPTED FOR NAVIGATION

(71) Applicant: Oticon A/S, Smørum (DK)

(72) Inventors: Thomas Lunner, Smørum (DK);
Martin Skoglund, Smørum (DK);
Fredrik Gustafsson, Linköping (SE)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 16/210,365

(22) Filed: Dec. 5, 2018

(65) Prior Publication Data
US 2019/0174237 A1    Jun. 6, 2019

(30) Foreign Application Priority Data

Dec. 6, 2017    (EP) .................................... 17205683

(51) Int. Cl.
*H04R 25/00*    (2006.01)
*G06F 3/01*    (2006.01)
(Continued)

(52) U.S. Cl.
CPC ............. *H04R 25/43* (2013.01); *G02C 11/06* (2013.01); *G06F 1/163* (2013.01); *G06F 3/011* (2013.01);
(Continued)

(58) Field of Classification Search
CPC .... H04R 25/43; H04R 1/1041; H04R 25/407; H04R 1/1083; H04R 5/027; H04R 5/04;
(Continued)

(56) References Cited

U.S. PATENT DOCUMENTS

| | | | |
|---|---|---|---|
| 2014/0098981 A1 | 4/2014 | Lunner et al. | |
| 2016/0165336 A1* | 6/2016 | Di Censo | G06F 3/165 |
| | | | 381/80 |
| 2016/0295323 A1* | 10/2016 | Yliaho | H04R 3/005 |

FOREIGN PATENT DOCUMENTS

| | | |
|---|---|---|
| EP | 2 813 175 A2 | 12/2014 |
| EP | 3 185 590 A1 | 6/2017 |

(Continued)

*Primary Examiner* — Ammar T Hamid
(74) *Attorney, Agent, or Firm* — Birch, Stewart, Kolasch & Birch, LLP

(57) ABSTRACT

A hearing system comprises a hearing device, e.g. a hearing aid, and is adapted for being worn by a user, the hearing system comprising a) an audio input unit configured to receive a multitude of audio signals comprising sound from a number of localized sound sources in an environment around the user, and b) a sensor unit configured to receive and/or provide sensor signals from one or more sensors, said one or more sensors being located in said environment and/or form part of said hearing system, and c) a first processor configured to generate and update over time data representative of a map of said environment of the user, said data being termed map data, said environment comprising a number of, stationary or mobile, landmarks, said landmarks comprising said number of localized sound sources, and said map data being representative of the physical location of said landmarks in the environment relative to the user, wherein the hearing system is configured to, preferably continuously, generate and update over time said map data based on said audio signals and said sensor signals. The invention further comprises a method.

19 Claims, 10 Drawing Sheets
(4 of 10 Drawing Sheet(s) Filed in Color)

(51) Int. Cl.
  *G02C 11/06* (2006.01)
  *G06F 1/16* (2006.01)
  *H04R 1/10* (2006.01)
  H04R 5/04 (2006.01)
  H04R 5/027 (2006.01)
  A61N 1/36 (2006.01)

(52) U.S. Cl.
  CPC ............. *G06F 3/013* (2013.01); *G06F 3/015* (2013.01); *H04R 1/1041* (2013.01); *H04R 25/407* (2013.01); *A61N 1/36038* (2017.08); *H04R 1/1083* (2013.01); *H04R 5/027* (2013.01); *H04R 5/04* (2013.01); *H04R 25/552* (2013.01); *H04R 25/554* (2013.01); *H04R 25/606* (2013.01); *H04R 2225/39* (2013.01); *H04R 2225/55* (2013.01); *H04R 2225/61* (2013.01); *H04R 2430/20* (2013.01); *H04R 2460/07* (2013.01)

(58) Field of Classification Search
  CPC ....... H04R 25/552; G02C 11/06; G06F 3/011; G06F 3/013; G06F 3/015; G06F 1/163; A61N 1/36038
  USPC ........................................................ 381/23.1
  See application file for complete search history.

(56) References Cited

FOREIGN PATENT DOCUMENTS

| EP | 3185590 A1 * | 6/2017 | ............. H04R 25/40 |
|----|---|---|---|
| WO | WO 2013/155217 A1 | 10/2013 | |
| WO | WO-2013155217 A1 * | 10/2013 | |

* cited by examiner

HEARING DEVICE OR SYSTEM ADAPTED FOR NAVIGATION

SUMMARY

The present disclosure relates to hearing devices, e.g. hearing aids, and in particular to the localization of a user wearing one or more hearing devices relative to two or more sound sources in a, typically confined, environment of the user.

It is proposed to configure a hearing device, e.g. a hearing aid, adapted to be worn by a user to generate and update over time data representative of a map of a current environment of the user (such data termed, 'the map data'). It is further proposed to configure the hearing device to localize the user relative to one or more sound sources in the physical environment of the user in interaction with the map data. The physical environment may e.g. be constituted by a room or other location comprising a multitude of physical objects, including one or more (localized) sound sources (e.g. persons, or other sound transmitters). The user's position in a given room or other location may be determined (estimated) in absolute or relative terms (e.g. coordinates). The user's position in a given room or other location (relative to one or more, possibly identified, sound sources) may be e.g. be displayed via a user interface, e.g. graphical user interface, e.g. on a remote control, e.g. a smartphone or similar device. A hearing device, e.g. a hearing aid, combining localization and mapping (e.g. using a Simultaneous Localization And Mapping (SLAM) approach) provides a significant improvement over prior art hearing devices, e.g. hearing aids, as discussed in the present disclosure. In an embodiment, maps based on radio field and magnetic disturbances are provided by the present disclosure. Thereby several parallel maps, e.g. based on observations from sensors of e.g. visual, audio, magnetic, radio field sources, etc., respectively, can be used to track the objects of interest (e.g. sound sources), and/or to localize a user relative to such objects. Using the spatial knowledge of objects (e.g. localized sound sources) around a user, object (location) specific head related transfer functions (HRTFs) for the left and right ears of the user can be determined (e.g. taken from a database) and applied to the respective sounds received from these objects (to avail the user of a sensation of the location of the sound sources relative to the user).

The disclosure proposes to provide a hearing device, e.g. a hearing aid, or a hearing system, e.g. a hearing aid system, comprising

- a microphone array comprising a multitude of microphones for picking up sound from an environment of a user wearing the hearing device or the hearing system and providing respective microphone signals;
- a beamformer filtering unit coupled to the microphone array and configured to provide one or more (e.g. a multitude of) beamformers directed towards one or more (e.g. two or more) sound sources of current interest in the environment of the user;
- a number (e.g. a multitude) of sensors (and/or access to data from such sensors) for providing sensor signals indicative of properties of sound sources or properties of the environment of the user;
- a processor for generating and updating over time data representative of a map of the physical location of the user wearing the hearing device or the hearing system relative to the sound sources and to possible other landmarks in the (physical) environment based on said sensor signals and said microphone signals;

wherein the hearing device or hearing system is configured to control and update over time the beamformer filtering unit in dependence of said map data.

Each beam former channel (that is the output for a specified direction of the beamformer filtering unit (providing an array of beamformers)), may comprises a single channel noise reduction filter (sometimes termed a post filter, e.g. a wiener filter, DNN/CNN) that further separates the target (in the case of a speech signal) from background noise in the noisy channel.

The hearing system may be embodied in one or more separate parts or devices in communication with each other, e.g. fully or partially integrated in a spectacle frame(s). The one or more separate parts or devices may comprise a behind the ear (BTE) part adapted for being located at or behind an ear of the user, and/or an in the ear (ITE) part adapted for being located at in an ear canal of the user, and/or a part configured to be fully or partially implanted in the head of the user, and a spectacle frame adapted for being worn at the eyes (and e.g. resting on the nose and/or ears) of the user and comprising a number of microphones and sensors, e.g. one or more of a movement sensor, an image sensor, a magnetic field sensor, a wireless signal strength sensor, and a sensor for picking up electric signals from the user's head, such as brain wave signals or EOG-potentials. The hearing system may comprise one or two hearing devices located at or in the ears of a user and a spectacle frame wherein or whereon one or more sensors are mounted. Communication between the one or two hearing devices and the spectacle frame (e.g. the sensors) may be wired or wireless.

A Hearing System:

In an aspect of the present application, a hearing system comprising a hearing device, e.g. a hearing aid, is provided. The hearing device is adapted for being worn by a user. The hearing system comprises

- an audio input unit configured to receive a multitude of audio signals comprising sound from a number of localized sound sources in an environment around the user,
- a sensor unit configured to receive and/or provide sensor signals from one or more sensors, said one or more sensors being located in said environment and/or form part of said hearing system, and
- a first processor configured to generate and update over time data representative of a map of said environment of the user, said data being termed map data, said environment comprising a number of, stationary or mobile, landmarks, said landmarks comprising said number of localized sound sources, and said map data being representative of the physical location of said landmarks in the environment relative to the user.

The hearing system is configured to, preferably continuously (or repeatedly, e.g. with predefined, e.g. regular, time intervals), generate and update over time said map data based on said audio signals and said sensor signals.

Thereby an improved hearing system may be provided.

The hearing device may comprise the audio input unit (or a part thereof). The hearing device may comprise the sensor unit (or a part thereof). The hearing device may comprise the first processor. Other partitions may be implemented. In an embodiment, the hearing audio input unit (or a part thereof) is embodied in a head worn structure, e.g. a frame of glasses. In an embodiment, the sensor unit (or a part thereof) is embodied in a head worn structure, e.g. a frame of glasses. In an embodiment, the first processor (or a part thereof) is embodied in a portable device, e.g. a smartphone or similar device, or in a head worn structure, e.g. a frame of glasses.

In an embodiment, the hearing device (or devices) is(are) embodied in a head worn structure, e.g. a frame of glasses.

The hearing system is thereby configured to estimate a present location of the user relative to the localized sound sources in dependence of the map data.

The term 'localized sound source' is in the present context taken to mean—at a given point in time—having a specific (as opposed to diffuse) origin in space, as is e.g. the case for a speech source originating from a person talking (or from a localized sound transducer, e.g. a loudspeaker). In an embodiment, the number N of, stationary or mobile, localized sound sources is larger than or equal to two, such as larger than or equal to three or four.

The term 'landmark' is in the present context taken to include fixed objects in the user's environment whose location can be estimated by sensors. Examples of such objects are localized sound sources (e.g. from a talking person or a loudspeaker). The term landmark may, however, also include localized areas of the environment exhibiting a characteristic (e.g. particularly small or large) value of a physical property, e.g. a field strength (such as a magnetic field or an electromagnetic signal, e.g. an FM-signal, etc.), e.g. due to physical objects (e.g. walls, windows, metallic structures, etc.) in the environment of the user.

The landmarks of a given environment comprise the localized sound sources, but may comprise additional objects or signal sources or, alternatively, be constituted solely by the sound sources.

The term 'processor' is used to indicate a digital processor that is suitable for executing processing algorithms, e.g. localization algorithms based on suitable input data.

In an embodiment, the current environment of the user is confined. A 'confined environment around the user wearing the hearing system' may e.g. be indoor, e.g. constituted by a room comprising different objects, e.g. furniture or devices, e.g. sound generating devices, or by a building comprising a multitude of rooms.

The hearing system may comprise a beamformer filtering unit coupled to the audio input unit and configured to provide one or more beamformers based on said multitude of audio signals. In an embodiment, the beamformer filtering unit is configured to provide a predefined number of beamformers, e.g. two or three or more (e.g. corresponding to all localized sound sources at a given time). In an embodiment, the beamformer filtering unit is adapted to provide that said number of beamformers is configurable, e.g. by the user, e.g. via a user interface. The beamformer filtering unit may be configured to provide that the predefined number of beamformers are directed towards localized sound sources of current interest, e.g. as indicated or determined via a user interface. In an embodiment, the beamformer filtering unit, e.g. one of the beamformers, comprises a linearly constrained minimum variance (LCMV) beamformer, e.g. an MVDR beamformer.

The hearing system may comprise an output unit for providing stimuli perceivable as sound to the user based on a processed electric output signal representing or comprising sound from one or more of said localized sound sources.

The first processor may be configured to allow a user to select at least one of said localized sound sources as a sound source of current interest. The first processor may be configured to allow the user to select more than one of the localized sound sources as sound sources of current interest, e.g. in a prioritized manner, e.g. indicating a relative weight between them, e.g. 60%, 20%, 20% for three sound sources of current interest.

The first processor may be configured to provide that at least one of said one or more beamformers is/are directed towards a respective one of said localized sound sources. In an embodiment, the first processor is configured to control and update over time the beamformer filtering unit in dependence of the map data, and to direct the one or more beamformers towards one or more of the localized sound sources in the environment of the user. The first processor may be configured to generate and update said beamformers to track (at least some, such as two or more, such as all) of said localized sound sources over time. In an embodiment, the hearing system is configured to allow a user to select any combination of said localized sound sources as provided by said beamformers as the processed electric output signal.

The processed electric output signal may comprise one of more of the localized sound sources based on the one or more beamformers.

The hearing system may be configured to automatically direct the beamformers towards the localized sound sources based on the map data, and optionally on a user input.

The hearing system may comprise a memory and be configured to store data in said memory representative of said approximate, time dependent map, allowing to track the movement of said user and/or said localized sound sources in said environment over time. The tracking is preferably provided regardless of head rotations or translations of landmarks and/or user (movements in the room). The hearing system may comprise appropriate movement sensors (e.g. a head tracker) allowing a tracking of the user's movement relative to a fixed or mobile coordinate system.

The audio input unit may comprise a microphone array comprising a multitude of microphones for picking up sound from said environment and providing respective microphone signals comprising sound from said number of localized sound sources and providing at least some of said multitude of audio signals. At least some of the multitude of microphones may be configured to be worn by the user. The multitude of microphones may e.g. comprise a microphone array. In an embodiment, the multitude of microphones are constituted by one or more microphone arrays. The microphone array or microphone arrays may be configured to be worn by the user. The multitude of microphones may comprise one or more stationary microphones, each e.g. located in a fixed position, e.g. on a table, relative to the user. The multitude of microphones may comprise one or more mobile microphones, e.g. located on an object, e.g. a person, moving relative to the user.

The hearing system may comprise a head worn frame or structure whereon at least some, such as all, of said multitude of microphones are located. In an embodiment, the head worn frame or structure comprises a spectacle frame or a headband.

The hearing system may comprise one or more wireless receivers, each comprising corresponding antenna and receiver circuitry, and each being configured to receive a part of the electromagnetic spectrum. In an embodiment, the receiver circuitry comprises an FM receiver. In an embodiment, the receiver circuitry comprises Bluetooth receiver, e.g. comprising a BLE receiver. In an embodiment, the hearing system is configured to receive at least one of said audio signals comprising sound from said number of localized sound sources via said antenna and receiver circuitry. In an embodiment, the receiver circuitry comprises a light-sensitive receiver, e.g. a receiver of infrared light (e.g. an IR photo diode).

In an embodiment, the sensor unit comprises a receiver of ultra sound, e.g. microphone, such as a specifically adapted microphone, such as a MEMS microphone.

The sensor unit may comprise one or more of an accelerometer, a gyroscope, and a magnetometer. The one or more additional sensors of the hearing system may e.g. comprise a magnetometer for mapping variations of a magnetic field in the environment. The one or more additional sensors may e.g. comprise an ultrasound sensor, e.g. for estimating a distance to a sound source. The one or more additional sensors of the hearing system may e.g. comprise an accelerometer, e.g. a 3D accelerometer. The one or more additional sensors of the hearing system may e.g. comprise a gyroscope, e.g. a 3D gyroscope.

The sensor unit may comprise one or more of said sensors, and wherein at least one of one or more sensors comprises an electrode for picking up body signals, e.g. Electroocculography (EOG) potentials and/or brainwave potentials, such as Electroencephalography (EEG) potentials.

The sensor unit may comprise one or more vision sensors, e.g. a camera. The one or more sensors may comprise a camera (e.g. directed towards a front direction relative to the user, e.g. towards landmarks in front of the user, (cf. e.g. [Davison; 2003], [Pax et al.; 2008], or [Lupton & Sukkarieh; 2008]). In an embodiment, the one or more sensors comprises a computer vision system. In an embodiment, the one or more sensors comprises a head mounted eye camera for eye tracking (see e.g. [Richardson & Spivey; 2004]).

The first processor may comprise a simultaneous localization and mapping (SLAM) algorithm. The underlying idea with SLAM (simultaneous localization and mapping) is to solve the two problems of localization and mapping jointly, as the name indicates, and it is basically all about relative measurements. One typically has an agent, robot, vehicle or such (in this disclosure, the 'robot' is the user), that is equipped with sensors measuring the environment as the it moves. Based on this sensor data, the task is then to estimate the location, direction, and other characteristics of the environment relative to a fixed frame (which can be defined arbitrarily, but usually as the first position and orientation of the robot) while at the same time use the estimated things in the environment to localize itself. The output data from such algorithms is the current state of the ego (the user) position, orientation, velocity, etc., and the relative position, direction, etc., of the things of interest in the environment. The estimation process is usually cast as a probabilistic inference problem and the parameters of interest are then treated as time-varying stochastic variables represented by state-space models. Briefly the SLAM inference problem includes:

Add new targets (landmarks) to the map (and possibly remove unlikely ones).
Associate measurements to targets.
Update the estimates as new data arrives.
Predict the estimates (with associated uncertainty) forward when there are no measurements.

A direction of arrival (DOA) of sound from the localized sound sources may be determined (as e.g. discussed in [Skoglund et al.; 2017]) and fed to the SLAM algorithm. In general, only DOA is provided and we don't know the distance between user and targets. In such case, a distance between the user and some of the landmarks may preferably be measured from two, or more, locations of the user (e.g. using ultra sound, or other 'radar like' techniques), and if combined with further information, assumptions, or knowledge, about the distance between (some of) the landmarks, then the position of the target sound sources can be estimated and at the same time the ego-position and orientation (pose) can be determined from the estimated target locations.

In an embodiment, the SLAM algorithm is configured to track everything in the scene relative to the ego-pose that is of interest in order to do beamforming relative to these targets. That is, the estimates from SLAM should input data to beamformers and other decision modules within the device.

The first processor may comprise a Kalman filter or an extended Kalman filter.

The first processor may comprise a face recognition algorithm for identifying one or more faces in the environment of the user (e.g. among the landmarks). In combination with mapping (e.g. SLAM), face recognition may enable the hearing system to identify a current location of one or more specific persons relative to the user (the hearing system e.g. comprising one or more hearing devices, possibly in combination with a frame of glasses wherein or whereon one or more sensors, including an image sensor, e.g. a camera, are mounted).

The hearing device may e.g. comprise a hearing aid, a headset, an earphone, an ear protection device or a combination thereof.

In an embodiment, the hearing device is adapted to provide a frequency dependent gain and/or a level dependent compression and/or a transposition (with or without frequency compression) of one or more frequency ranges to one or more other frequency ranges, e.g. to compensate for a hearing impairment of a user. In an embodiment, the hearing device comprises a signal processor for enhancing the input signals and providing a processed output signal.

In an embodiment, the hearing device comprises an output unit for providing a stimulus perceived by the user as an acoustic signal based on a processed electric signal. In an embodiment, the output unit comprises a number of electrodes of a cochlear implant or a vibrator of a bone conducting hearing device. In an embodiment, the output unit comprises an output transducer. In an embodiment, the output transducer comprises a receiver (loudspeaker) for providing the stimulus as an acoustic signal to the user. In an embodiment, the output transducer comprises a vibrator for providing the stimulus as mechanical vibration of a skull bone to the user (e.g. in a bone-attached or bone-anchored hearing device).

In an embodiment, the hearing device comprises an input unit for providing an electric input signal representing sound. In an embodiment, the input unit comprises an input transducer, e.g. a microphone, for converting an input sound to an electric input signal. In an embodiment, the input unit comprises a wireless receiver for receiving a wireless signal comprising sound and for providing an electric input signal representing said sound.

In an embodiment, the hearing device comprises a directional microphone system (e.g. a beamformer filtering unit) adapted to spatially filter sounds from the environment, and thereby enhance a target acoustic source among a multitude of acoustic sources in the local environment of the user wearing the hearing device. In an embodiment, the directional system is adapted to detect (such as adaptively detect) from which direction a particular part of the microphone signal originates. This can be achieved in various different ways as e.g. described in the prior art. In hearing devices, a microphone array beamformer is often used for spatially attenuating background noise sources. Many beamformer variants can be found in literature. The present disclosure is not limited to one specific type of beamformer, but may be utilized in connection with any kind as determined by the practical application. The minimum variance distortionless response (MVDR) beamformer is an example of a linearly constrained minimum variance (LCMV) beamformer. Other beamformers from this group than the MVDR beamformer may be used, e.g. a multi-channel Wiener filter (MWF) beamformer. In an embodiment, a quantization-aware beamforming scheme, which uses a modified cross power spectral density (CPSD) of the system noise including the quantization noise (QN), is proposed. The minimum variance distortionless response (MVDR) beamformer is, however, widely used in microphone array signal processing. Ideally the MVDR beamformer keeps the signals from the target direction (also referred to as the look direction) unchanged, while attenuating sound signals from other directions maximally. The generalized sidelobe canceller (GSC) structure is an equivalent representation of the MVDR beamformer offering computational and numerical advantages over a direct implementation in its original form. Several textbooks and reviews of different beamformers exist, cf. e.g. [Lorenz & Boyd; 2005] as an example of the latter.

In an embodiment, the hearing device comprises an antenna and transceiver circuitry (e.g. a wireless receiver) for wirelessly receiving a direct electric input signal from another device, e.g. from an entertainment device (e.g. a TV-set), a communication device, a wireless microphone, or another hearing device. In an embodiment, the direct electric input signal represents or comprises an audio signal and/or a control signal and/or an information signal. In an embodiment, the hearing device comprises demodulation circuitry for demodulating the received direct electric input to provide the direct electric input signal representing an audio signal and/or a control signal e.g. for setting an operational parameter (e.g. volume) and/or a processing parameter of the hearing device. In general, a wireless link established by antenna and transceiver circuitry of the hearing device can be of any type. In an embodiment, the wireless link is established between two devices, e.g. between an entertainment device (e.g. a TV) and the hearing device, or between two hearing devices, e.g. via a third, intermediate device (e.g. a processing device, such as a remote control device, a smartphone, etc.). In an embodiment, the wireless link is used under power constraints, e.g. in that the hearing device is or comprises a portable (typically battery driven) device. In an embodiment, the wireless link is a link based on near-field communication, e.g. an inductive link based on an inductive coupling between antenna coils of transmitter and receiver parts. In another embodiment, the wireless link is based on far-field, electromagnetic radiation. In an embodiment, the communication via the wireless link is arranged according to a specific modulation scheme, e.g. an analogue modulation scheme, such as FM (frequency modulation) or AM (amplitude modulation) or PM (phase modulation), or a digital modulation scheme, such as ASK (amplitude shift keying), e.g. On-Off keying, FSK (frequency shift keying), PSK (phase shift keying), e.g. MSK (minimum shift keying), or QAM (quadrature amplitude modulation), etc.

In an embodiment, the communication between the hearing device and the other device is in the base band (audio frequency range, e.g. between 0 and 20 kHz). Preferably, communication between the hearing device and the other device is based on some sort of modulation at frequencies above 100 kHz. Preferably, frequencies used to establish a communication link between the hearing device and the other device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). In an embodiment, the wireless link is based on a standardized or proprietary technology. In an embodiment, the wireless link is based on Bluetooth technology (e.g. Bluetooth Low-Energy technology).

In an embodiment, the hearing device is a portable device, e.g. a device comprising a local energy source, e.g. a battery, e.g. a rechargeable battery.

In an embodiment, the hearing device comprises a forward or signal path between an input unit (e.g. an input transducer, such as a microphone or a microphone system and/or direct electric input (e.g. a wireless receiver)) and an output unit, e.g. an output transducer. In an embodiment, the signal processor is located in the forward path. In an embodiment, the signal processor is adapted to provide a frequency dependent gain according to a user's particular needs. In an embodiment, the hearing device comprises an analysis path comprising functional components for analyzing the input signal (e.g. determining a level, a modulation, a type of signal, an acoustic feedback estimate, etc.). In an embodiment, some or all signal processing of the analysis path and/or the signal path is conducted in the frequency domain. In an embodiment, some or all signal processing of the analysis path and/or the signal path is conducted in the time domain.

In an embodiment, an analogue electric signal representing an acoustic signal is converted to a digital audio signal in an analogue-to-digital (AD) conversion process, where the analogue signal is sampled with a predefined sampling frequency or rate $f_s$, $f_s$ being e.g. in the range from 8 kHz to 48 kHz (adapted to the particular needs of the application) to provide digital samples $x_n$ (or x[n]) at discrete points in time $t_n$ (or n), each audio sample representing the value of the acoustic signal at $t_n$ by a predefined number $N_b$ of bits, $N_b$ being e.g. in the range from 1 to 48 bits, e.g. 24 bits. Each audio sample is hence quantized using $N_b$ bits (resulting in $2^{N_b}$ different possible values of the audio sample). A digital sample x has a length in time of $1/f_s$, e.g. 50 µs, for $f_s$=20 kHz. In an embodiment, a number of audio samples are arranged in a time frame. In an embodiment, a time frame comprises 64 or 128 audio data samples. Other frame lengths may be used depending on the practical application.

In an embodiment, the hearing devices comprise an analogue-to-digital (AD) converter to digitize an analogue input (e.g. from an input transducer, such as a microphone) with a predefined sampling rate, e.g. 20 kHz. In an embodiment, the hearing devices comprise a digital-to-analogue (DA) converter to convert a digital signal to an analogue output signal, e.g. for being presented to a user via an output transducer.

In an embodiment, the hearing device, e.g. the microphone unit, and or the transceiver unit comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit for converting a time variant input signal to a (time variant) signal in the (time-)frequency domain. In an embodiment, the frequency range considered by the hearing device from a minimum frequency $f_{min}$ to a maximum frequency $f_{max}$ comprises a part of the typical human audible frequency range from 20 Hz to 20 kHz, e.g. a part of the range from 20 Hz to 12 kHz. Typically, a sample rate $f_s$ is larger than or equal to twice the maximum frequency $f_{max}$, $f_s \geq 2f_{max}$. In an embodiment, a signal of the forward and/or analysis path of the hearing device is split into a number NI of frequency bands (e.g. of uniform width), where NI is e.g. larger than 5, such as larger than 10, such as larger than 50, such as larger than 100, such as larger than 500, at least some of which are processed individually. In an embodiment, the hearing device is/are adapted to process a signal of the forward and/or analysis path in a number NP of different frequency channels (NP≤NI). The frequency channels may be uniform or non-uniform in width (e.g. increasing in width with frequency), overlapping or non-overlapping.

In an embodiment, the hearing device comprises a number of detectors configured to provide status signals relating to a current physical environment of the hearing device (e.g. the current acoustic environment), and/or to a current state of the user wearing the hearing device, and/or to a current state or mode of operation of the hearing device. Alternatively or additionally, one or more detectors may form part of an external device in communication (e.g. wirelessly) with the hearing device. An external device may e.g. comprise another hearing device, a remote control, and audio delivery device, a telephone (e.g. a Smartphone), an external sensor, etc.

In an embodiment, one or more of the number of detectors operate(s) on the full band signal (time domain). In an embodiment, one or more of the number of detectors operate(s) on band split signals ((time-) frequency domain), e.g. in a limited number of frequency bands.

In an embodiment, the number of detectors comprises a level detector for estimating a current level of a signal of the forward path. In an embodiment, the predefined criterion comprises whether the current level of a signal of the forward path is above or below a given (L-)threshold value. In an embodiment, the level detector operates on the full band signal (time domain). In an embodiment, the level detector operates on band split signals ((time-) frequency domain).

In a particular embodiment, the hearing device comprises a voice detector (VD) for estimating whether or not (or with what probability) an input signal comprises a voice signal (at a given point in time). A voice signal is in the present context taken to include a speech signal from a human being. It may also include other forms of utterances generated by the human speech system (e.g. singing). In an embodiment, the voice detector unit is adapted to classify a current acoustic environment of the user as a VOICE or NO-VOICE environment. This has the advantage that time segments of the electric microphone signal comprising human utterances (e.g. speech) in the user's environment can be identified, and thus separated from time segments only (or mainly) comprising other sound sources (e.g. artificially generated noise). In an embodiment, the voice detector is adapted to detect as a VOICE also the user's own voice. Alternatively, the voice detector is adapted to exclude a user's own voice from the detection of a VOICE.

In an embodiment, the hearing device comprises an own voice detector for estimating whether or not (or with what probability) a given input sound (e.g. a voice, e.g. speech) originates from the voice of the user of the system. In an embodiment, a microphone system of the hearing device is adapted to be able to differentiate between a user's own voice and another person's voice and possibly from NON-voice sounds.

In an embodiment, the number of detectors comprises a movement detector, e.g. an acceleration sensor. In an embodiment, the movement detector is configured to detect movement of the user's facial muscles and/or bones, e.g. due to speech or chewing (e.g. jaw movement) and to provide a detector signal indicative thereof.

The number of detectors may comprise bio sensors, e.g. comprising electrodes for picking up signals from the user's body. Examples of such signals may be EOG, EEG, MEG, etc.

In an embodiment, the hearing device comprises a classification unit configured to classify the current situation based on input signals from (at least some of) the detectors, and possibly other inputs as well. In the present context 'a current situation' is taken to be defined by one or more of
a) the physical environment (e.g. including the current electromagnetic environment, e.g. the occurrence of electromagnetic signals (e.g. comprising audio and/or control signals) intended or not intended for reception by the hearing device, or other properties of the current environment than acoustic);
b) the current acoustic situation (input level, feedback, etc.), and
c) the current mode or state of the user (movement, temperature, cognitive load, etc.);
d) the current mode or state of the hearing device (program selected, time elapsed since last user interaction, etc.) and/or of another device in communication with the hearing device.

In an embodiment, the hearing device further comprises other relevant functionality for the application in question, e.g. compression, noise reduction, etc.

In an embodiment, the hearing device comprises a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof.

Use:

In an aspect, use of a hearing device as described above, in the 'detailed description of embodiments' and in the claims, is moreover provided. In an embodiment, use is provided in a system comprising audio distribution. In an embodiment, use is provided in a system comprising one or more hearing aids (e.g. hearing instruments), headsets, ear phones, active ear protection systems, etc., e.g. in handsfree telephone systems, teleconferencing systems, public address systems, karaoke systems, classroom amplification systems, etc.

A Method:

In an aspect, a method of operating a hearing system comprising a hearing device, e.g. a hearing aid, the hearing device being adapted for being worn by a user is furthermore provided by the present application. The method comprises
  receiving audio signals comprising sound from said number of localized sound sources in an environment around the user,
  receiving and/or providing sensor signals from one or more sensors, said one or more sensors being located in said environment and/or form part of said hearing system,
  generating and updating over time data representative of a map of said environment of the user, said data being termed map data, said environment comprising a number of, stationary or mobile, landmarks, said landmarks comprising a number of localized sound sources, and said map data being representative of the physical location of said landmarks in the environment relative to the user; and generating and updating over time said map data based on said audio signals and said sensor signals.

It is intended that some or all of the structural features of the system and devices described above, in the 'detailed description of embodiments' or in the claims can be combined with embodiments of the method, when appropriately substituted by a corresponding process and vice versa. Embodiments of the method have the same advantages as the corresponding systems and devices.

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

A Computer Program:

A computer program (product) comprising instructions which, when the program is executed by a computer, cause the computer to carry out (steps of) the method described above, in the 'detailed description of embodiments' and in the claims is furthermore provided by the present application.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Hearing System:

In a further aspect, a hearing system comprising a hearing device as described above, in the 'detailed description of embodiments', and in the claims, AND an auxiliary device is moreover provided.

In an embodiment, the hearing system is adapted to establish a communication link between the hearing device and the auxiliary device to provide that information (e.g. control and status signals, possibly audio signals) can be exchanged or forwarded from one to the other.

In an embodiment, the hearing system comprises an auxiliary device, e.g. a remote control, a smartphone, or other portable or wearable electronic device, such as a smartwatch or the like.

In an embodiment, the auxiliary device is or comprises a remote control for controlling functionality and operation of the hearing device(s). In an embodiment, the function of a remote control is implemented in a smartphone, the smartphone possibly running an APP allowing to control the functionality of the audio processing device via the smartphone (the hearing device(s) comprising an appropriate wireless interface to the smartphone, e.g. based on Bluetooth or some other standardized or proprietary scheme).

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing device.

In an embodiment, the auxiliary device is or comprises another hearing device. In an embodiment, the hearing system comprises two hearing devices adapted to implement a binaural hearing system, e.g. a binaural hearing aid system.

An APP:

In a further aspect, a non-transitory application, termed an APP, is furthermore provided by the present disclosure. The APP comprises executable instructions configured to be executed on an auxiliary device to implement a user interface for a hearing device or a hearing system described above in the 'detailed description of embodiments', and in the claims. In an embodiment, the APP is configured to run on an auxiliary device, e.g. a cellular phone, such as a smartphone, or on another portable device allowing communication with said hearing device or said hearing system.

In an embodiment, the hearing system is configured to allow a user to view a location of sound sources in the environment relative to the user (as e.g. shown in FIG. 2) via the user interface, e.g. of the smartphone. In an embodiment, the sound sources displayed by the user interface are determined according to the present disclosure based on map data, e.g. using a SLAM algorithm. In an embodiment, the user's movement over time relative to the sound sources are illustrated by the user interface. In an embodiment, the user interface is configured to allow the user to indicate which one (or more) of the shown sound sources that are of a current interest (e.g. by clicking on the sound source symbol in question). In an embodiment, the hearing system (including the user interface) is configured to allow a user to indicate a weight of each sound source, if more than one is selected, each weight being applied to the relevant sound source when presented to the user via an output unit of the hearing device. In other words, the hearing system (including the auxiliary device) is configured to transmit information about the selected sound source(s) (and possibly their mutual relative weights) to the hearing device (or to left and right hearing devices) of the hearing system to allow them to focus the processed output signals presented to the ear(s) of the user on the selected sound sources.

Definitions

In the present context, a 'hearing device' refers to a device, such as a hearing aid, e.g. a hearing instrument, or an active ear-protection device, or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing device may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing device may comprise a single unit or several units communicating electronically with each other. The loudspeaker may be arranged in a housing together with other components of the hearing device, or may be an external unit in itself (possibly in combination with a flexible guiding element, e.g. a dome-like element).

More generally, a hearing device comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing devices, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing device and/or for storing information (e.g. processed information, e.g. provided by the signal processing circuit), e.g. for use in connection with an interface to a user and/or an interface to a programming device. In some hearing devices, the output unit may comprise an output transducer, such as e.g. a loudspeaker for providing an air-borne acoustic signal or a vibrator for providing a structure-borne or liquid-borne acoustic signal. In some hearing devices, the output unit may comprise one or more output electrodes for providing electric signals (e.g. a multi-electrode array for electrically stimulating the cochlear nerve).

In some hearing devices, the vibrator may be adapted to provide a structure-borne acoustic signal transcutaneously or percutaneously to the skull bone. In some hearing devices, the vibrator may be implanted in the middle ear and/or in the inner ear. In some hearing devices, the vibrator may be adapted to provide a structure-borne acoustic signal to a middle-ear bone and/or to the cochlea. In some hearing devices, the vibrator may be adapted to provide a liquid-borne acoustic signal to the cochlear liquid, e.g. through the oval window. In some hearing devices, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A hearing device, e.g. a hearing aid, may be adapted to a particular user's needs, e.g. a hearing impairment. A configurable signal processing circuit of the hearing device may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing device via an interface to a programming device (fitting system), and used by a processing algorithm executed by the configurable signal processing circuit of the hearing device.

A 'hearing system' refers to a system comprising one or two hearing devices, and a 'binaural hearing system' refers to a system comprising two hearing devices and being adapted to cooperatively provide audible signals to both of the user's ears. Hearing systems or binaural hearing systems may further comprise one or more 'auxiliary devices', which communicate with the hearing device(s) and affect and/or benefit from the function of the hearing device(s). Auxiliary devices may be e.g. remote controls, audio gateway devices, mobile phones (e.g. smartphones), or music players. Hearing devices, hearing systems or binaural hearing systems may e.g. be used for compensating for a hearing-impaired person's loss of hearing capability, augmenting or protecting a normal-hearing person's hearing capability and/or conveying electronic audio signals to a person. Hearing devices or hearing systems may e.g. form part of or interact with public-address systems, active ear protection systems, handsfree telephone systems, car audio systems, entertainment (e.g. karaoke) systems, teleconferencing systems, classroom amplification systems, etc.

Embodiments of the disclosure may e.g. be useful in applications such as portable hearing devices.

BRIEF DESCRIPTION OF DRAWINGS

The patent or application file contains at least one color drawing. Copies of this patent or patent application publication with color drawing will be provided by the USPTO upon request and payment of the necessary fee.

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Figure 1A:
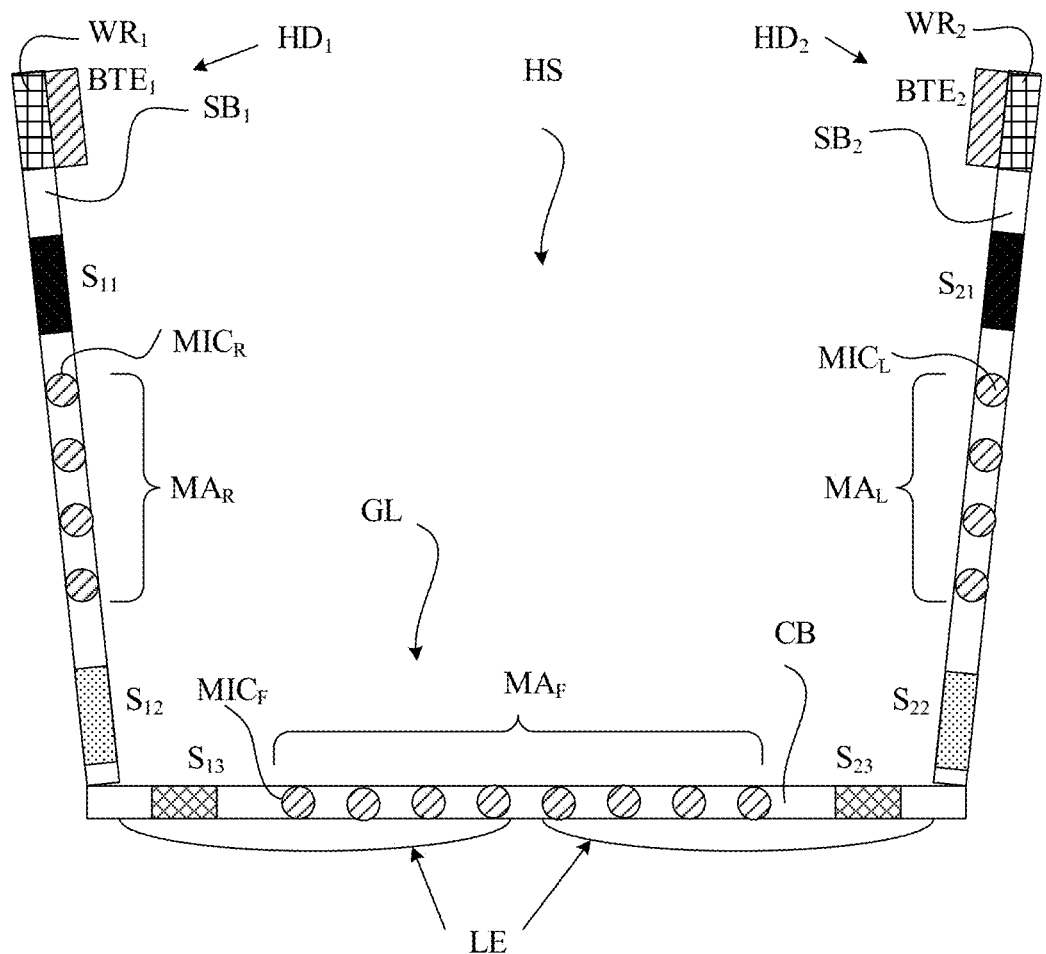
FIGS. 1A and 1B show respective top and front views of an embodiment of a hearing system according to the present disclosure comprising a sensor integration device configured to be worn on the head of a user, e.g. comprising a head worn carrier, such as a spectacle frame.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of hearing systems, e.g. comprising one or more hearing devices, e.g. hearing aids, in particular to a hearing device or devices adapted to provide an improved sensation of sound sources in a confined environment, e.g. indoor, of a user wearing the hearing device.

The present application deals with a hearing system comprising sensor integration device (e.g. forming part of, such as integrated in, or in communication with a hearing device) that enhances the sounds in the user's focus.

In an embodiment, the hearing system, e.g. a hearing device, comprises an indoor navigation device for user localization, multiple target mapping and tracking of sound sources around the user. In an embodiment, the hearing system is configured to allow the use of eye-gaze tracking of the user to enhance/augment a sound source of the user's (current) focus.

Listeners/hearing aid users may have problems segregating, following and focusing attention to a given dynamic auditory object in a scene of multiple acoustic objects. This is especially true for hard-of-hearing listeners. In spite of the ability of modern hearing aids to create some separation of the sources, e.g. using multiple microphone beamforming (and further noise reduction), there is a need for augmenting the sounds that are in the users focus.

In other words, the user needs help to track multiple acoustic objects, to segregate these, and to indicate which one is of interest for the moment, and for auditory display for a natural perception of the sound scene.

The solution consists of four elements:
A. User localization and multiple target mapping and tracking (SLAM)
B. Determining the (sound) source in user's focus of attention for the moment
C. Augmenting/enhancing the source in the user's focus
D. Calculating the auditory display (sound to be presented to the left and right ears) of the enhanced sound scene and transmitting this to a pair of hearing aids.

Figure 1B:
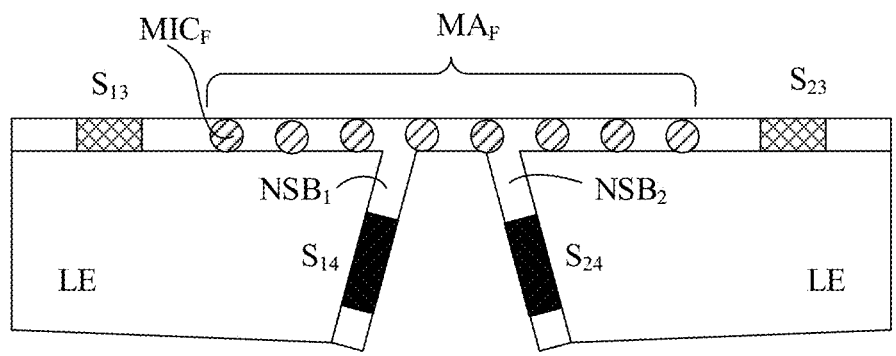

FIGS. 1A and 1B illustrate respective top and front views of an embodiment of a hearing system according to the present disclosure comprising a sensor integration device configured to be worn on the head of a user, e.g. comprising a head worn carrier, such as a spectacle frame.

FIG. 1A and FIG. 1B show respective (schematic) top and front views of a spectacle frame for carrying an embodiment of a hearing system according to the present disclosure. The hearing system comprises left and right hearing devices and a number of sensors mounted on the spectacle frame. The hearing system (HS) comprises a number of sensors $S_{1i}$, $S_{2i}$, (i=1, . . . , $N_S$) associated with (e.g. forming part of or connected to) left and right hearing devices ($HD_1$, $HD_2$), respectively. Ns is the number of sensors located on each side of the frame (in the example of FIG. 1A, 1B assumed to be symmetric, which need not necessary be so, though). The first, second, third, and fourth sensors $S_{11}$, $S_{12}$, $S_{13}$, $S_{14}$ and $S_{21}$, $S_{22}$, $S_{23}$, $S_{24}$ are mounted on a spectacle frame of the glasses (GL). In the embodiment of FIG. 1A, sensors $S_{11}$, $S_{12}$ and $S_{21}$, $S_{22}$ are mounted on the respective sidebars ($SB_1$ and $SB_2$), whereas sensors $S_{13}$ and $S_{23}$ are mounted on the cross bar (CB) having hinged connections to the right and left side bars ($SB_1$ and $SB_2$). Finally, sensors $S_{14}$ and $S_{24}$ are mounted on first and second nose sub-bars ($NSB_1$, $NSB_2$) extending from the cross bar (CB) and adapted for resting on the nose of the user. Glasses or lenses (LE) of the spectacles are mounted on the cross bar (CB) and nose sub-bars ($NSB_1$, $NSB_2$). The left and right hearing devices ($HD_1$, $HD_2$) comprises respective BTE-parts ($BTE_1$, $BTE_2$), and may e.g. further comprise respective ITE-parts ($ITE_1$, $ITE_2$). The ITE-parts may e.g. comprise electrodes for picking up body signals from the user, e.g. forming part of sensors $S_{1i}$, $S_{2i}$ (l=1, . . . $N_S$) for monitoring physiological functions of the user, e.g. brain activity or eye movement activity or temperature. Likewise, the one or more of the sensors on the spectacle frame may comprise electrodes for picking up body signals from the user. In an embodiment, sensors S11, S14 and S21, S24 (black rectangles) may represent sensor electrodes for picking up body signals e.g. Electroocculography (EOG) potentials and/or brainwave potentials, e.g. Electroencephalography (EEG) potentials, cf. e.g. EP3185590A1. The sensors mounted on the spectacle frame may e.g. comprise one or more of an accelerometer, a gyroscope, a magnetometer, a radar sensor, an eye camera (e.g. for monitoring pupillometry), a camera (e.g. for imaging objects of the environment of the user), or other sensors for localizing or contributing to localization of a sound source (or other landmark) of interest to the user wearing the hearing system. The sensors ($S_{13}$, $S_{23}$) located on the cross bar (CB) and/or sensors (e.g. $S_{12}$, $S_{22}$) located on the side bars ($SB_1$, $SB_2$) may e.g. include one or more cameras or radar or ultra sound sensors for monitoring the environment. The hearing system further comprises a multitude of microphones, here configured in three separate microphone arrays ($MA_R$, $MA_L$, $MA_F$) located on the right, left side bars and on the (front) cross bar, respectively. Each microphone array ($MA_R$, $MA_L$, $MA_F$) comprises a multitude of microphones ($MIC_R$, $MIC_L$, $MIC_F$, respectively), here four, four and eight, respectively. The microphones may form part of the hearing system (e.g. associated with the right and left hearing devices ($HD_1$, $HD_2$), respectively, and contribute to localise and spatially filter sound from the respective sound sources of the environment around the user, cf. e.g. our co-pending European patent application number 17179464.7 filed with the European Patent Office on $4^{th}$ of Jul. 2017 and having the title Direction Of Arrival Estimation In Miniature Devices Using A Sound Sensor Array.

A. User Localization and Multiple Target Mapping and Tracking (SLAM)

Figure 2:
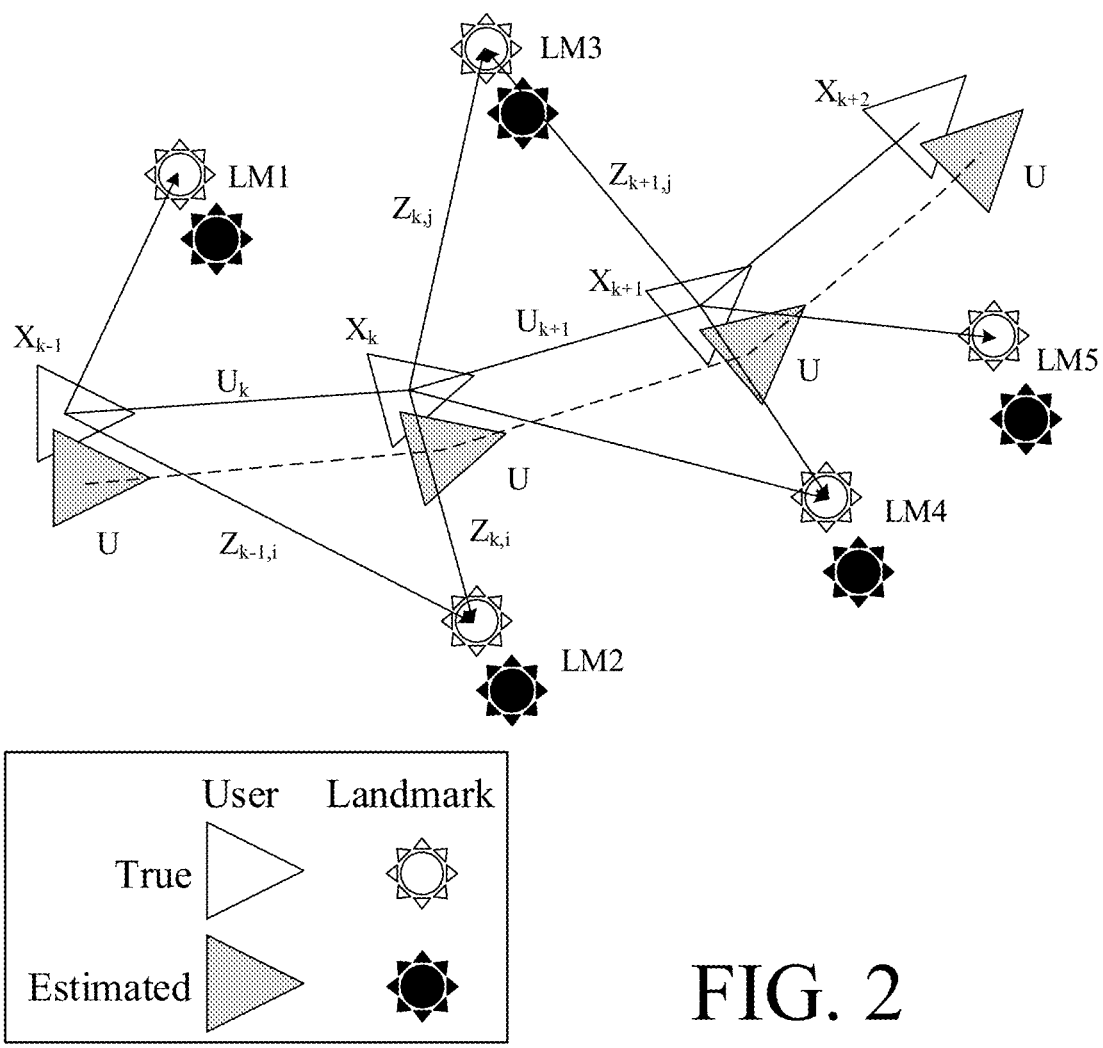
FIG. 2 illustrates a simultaneous localization and mapping technique where several time-stamps of the localization of the user (triangles) are indicated during movement in space.

In SLAM the problem of localization (of the user) and mapping (of the targets) is solved simultaneously, and can take a multitude of sensor inputs to build up the localization and mapping. In FIG. 2, triangles may represent the true and estimated position (location) and orientation of the user, respectively. In an embodiment, the hearing system is configured to estimate a location and orientation of landmarks as well. In an embodiment, only the location is estimated (while its orientation is ignored). The orientation of landmarks can e.g. be estimated with a camera (as one of the sensors). The orientation of a landmark representing a sound source (e.g. a person speaking) may be useful for qualifying eye gaze estimation, as it may be less likely that the user attends to a source that is not facing the user.

Figure 3:
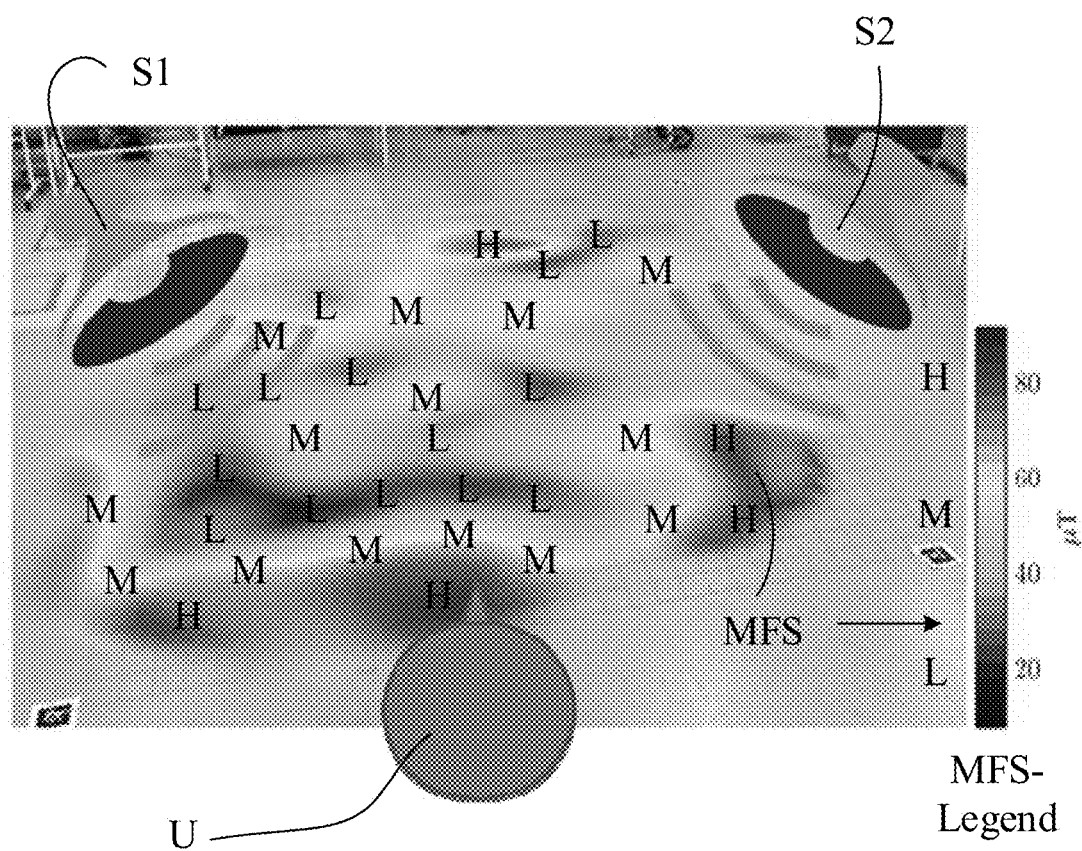
FIG. 3 shows map data created by a magnetic field sensor reflecting variations in the magnetic field in an environment comprising two localized sound sources, and a listener (user)

FIG. 2 shows a simultaneous localization and mapping (SLAM) technique where several time-stamps of the localization of the user (triangles) are indicated during movement in space. The time-stamps are represented by index k. In FIG. 2, a movement (track) of the user from left to right (cf. locations $X_{k-1}$, $X_k$, $X_{k+1}$, $X_{k+2}$, of the user (represented by white triangles) in an environment comprising a number of landmarks m (e.g. LM1, . . . LM5) represented by sun symbols). The user's estimated and true location at a given point in time is indicated by grey shaded and open (unshaded, white) triangles, respectively. The estimated and true location of the landmarks (LM1-LM5) at a given point in time is indicated by solid (black) and open (white) sun symbols, respectively. The user can be stationary (sitting at a dinner table) or moving around (walking around in a museum). The landmarks can be static sound objects with a given direction (direction of arrival, DOA) relative to and distance from the listener, but they can also be dynamic (e.g. represented by persons talking, while moving around in a museum). The DOA e.g. can be determined from hearing aid microphone arrays (e.g. worn by a user, cf. FIG. 1A, 1B), from a number of connected microphones at a table or mounted in a room, or from remote microphones close to the sound sources (e.g. talkers each wearing a wireless microphone). Other static landmarks can comprise objects whose location can be estimated from sensors capable of sensing physical properties of the objects in question (e.g. its magnetic properties). Such objects may be identified in a map created by a sensor over time, see e.g. the magnetometer map in FIG. 3, that maps out the static magnetic variations in a room. Other static landmarks can be beacons (e.g. BT transmitters, short wide band pulses of radio, or magnet field transmitters), or the signals from remote static FM transmitters (FM radio band, creating a variation of the received signal strength in the room), or the signal strength from WiFi transmitters across a room. FIG. 3 shows a user in a room with two sound sources and a listener (user).

In embodiments, one or more image sensors, e.g. cameras, may be used to contribute to the mapping of the environment, e.g. one or more of
  a monocular camera (cf. e.g. [Davison; 2003]),
  a stereo camera (cf. e.g. [Pax et al.; 2008]), and
  a combination of an IMU and a monocular or a stereo camera (cf. e.g. [Lupton; 2008])

FIG. 3 shows map data created by a magnetic field sensor reflecting variations in the magnetic field in an environment comprising two localized sound sources, and a listener (user). The legend (spanning magnetic field strengths from 0 to 100 micro Tesla (µT)) is indicated in the right part of the graph (cf. column denoted 'MFS-legend). The same information is intended to be (coarsely) given by letters L, M, H indicating a relatively low, middle and relatively high field strength, respectively, in the depicted part of the environment of the user. L, M and H and e.g. be associated with approximately 20, 50 and 80 µT, respectively. The magnetic field strength (assumed to relatively static) can be used to identify a present location of a landmark (sound source, S1, S2) and/or the user (U), possibly in combination with other location dependent data.

EXAMPLE

An example of how the combination of sensors can be used in hearing aids is provided in the following. A method for indoor localization using opportunistic signals, e.g., FM radio in the 88-106 MHz band, together with inertial sensors is proposed.

Input:

Antenna and receiver circuitry in the hearing device, which are sensitive to 88-106 MHz FM bands (and possibly other additional bands) provides electric signals representing the FM signal at the hearing device.

Inertial sensors, that is, 3D accelerometer, 3D gyroscopes, and 3D magnetometers located in the hearing device provides sensor signals representative of linear and angular movement of the use as well as the magnetic field strength at the hearing device.

Output:

A map reflecting the received signal strength (RSS) of the FM signal, with uncertainties, of the radio environment of the visited locations for the selected frequencies (recorded during the movement of the user in the environment).

2D Position and 3D orientation of the hearing device with their corresponding uncertainty estimates.

There are several reasons to why it is interesting to study the opportunistic use of multi-frequency RSS for indoor localization. FM radio and TV signals are present almost everywhere and may therefore be utilized in e.g., first responder scenarios where pre-installed infrastructure cannot be trusted. Signal fading characteristics depends on frequency, and the surrounding environment, resulting in different RSS maps. These maps combined are naturally more informative than a single map alone.

A radio signal interacts with the physical environment in an extremely complex manner. It experiences a distance dependent attenuation (path loss) and the radio signal is reflected off different objects, diffracted around obstacles, and scattered off objects. Hence, the receiver will receive many (distorted and delayed) signal components. The constructive and destructive addition of these multipath components is the cause for the rapid fluctuations as a function of spatial displacement of the RSS values that are typical for all non-line-of-sight (NLOS) wireless radio channels which is the typical situation here. This phenomenon is called multipath fading. Apart from the multipath fading, also antenna orientation and shadowing affect the measurements.

Radio Environment Model

A RSS fingerprint is a set of mean signal strength values collected at different frequencies at different positions. Each frequency in the RSS fingerprint vector is assumed to be a function of its position in 2D space. In indoor localization, fingerprints are measured beforehand and used as a map. Another alternative is to utilize signal source locations, e.g. WiFi access points (APs), and a radio channel path loss model which describes how the signal attenuates as a function of distance to each source. In some cases, these methods do not work, for instance, if the map cannot be obtained beforehand, the radio source locations are not known, or if it is not meaningful to describe the signal using a path loss model. An alternative then is to model the RSS with a Gaussian Process (GP) which locally describes how the signal RSS varies as a function of the 2D position.

Inertial Navigation

Inertial navigation is a well-known technique used for computing position, velocity, orientation, and other quantities by the means of inertial sensors. In this application, inertial navigation is used to compute a position and orientation estimate. Without additional information, the errors of the position and orientation estimates grows quadratically and linearly, respectively.

RSS SLAM

Simultaneous localization and mapping (SLAM) is a methodology to jointly estimate the position of mobile sensors and a map of the signals that the sensors measure. In this application, the RSS map is represented as a GP over the traversed area. Inertial navigation is used to provide position and orientation estimates which are corrected using the RSS map in a statistical filtering framework. These corrections are most useful when an area is revisited as it can potentially remove the errors completely.

The processing for RSS SLAM comprises the following steps:

Provide radio and IMU data
Preprocess
RSS SLAM
Position and Map

In SLAM static landmarks/sources are treated differently than dynamic/moving sources. Therefore, five different use scenarios are described below.

Table 1 below describes a number of sensors that may be used in different combinations to solve the SLAM problem for the five different scenarios depending on whether sound sources are stationary or mobile, whether the listener (user) is stationary of mobile, and whether the SLAM solution considers a single room or a building (with several rooms).

The sensors are arranged in the table according to the following groups:

3D Accelerometer,
3D Gyroscope,
3D Magnetometer,
EEG/EOG electrodes,
Augmenting device (MEMS) microphones,
Radio antenna receiver,
Radio antenna transmitter,
Magnetic antenna (T-coil),
Bluetooth transmitter,
Bluetooth receiver,
Ultra sound sensors,
Front camera
Eye camera

TABLE 1

A number of sensors that may be used in different combinations to solve the SLAM problem.

| Sensor/input type | Signals | Quantities of interest |
|---|---|---|
| 3D Accelerometer 1 per ear or multiple | Linear acceleration vector Centrifugal force Euler force | Linear acceleration Linear velocity Position Direction of gravity vector Magnitude of gravity vector Movement detection - Walking, running . . . Anomalies . . . |

TABLE 1-continued

A number of sensors that may be used in different combinations to solve the SLAM problem.

| Sensor/input type | Signals | Quantities of interest |
|---|---|---|
| 3D Gyroscope 1 per ear or multiple | Angular velocity | Angular velocity Short time local orientation Movement detection/classification - Walking, running . . . Anomalies |
| 3D Magnetometer 1 per ear or multiple | Magnetic field | Local magnetic field vector Local magnetic field vector magnitude Magnetic disturbances/targets characteristics Magnetic field variation →linear velocity, position |
| EEG/EOG electrodes 2 per ear or multiple | Electric field and other disturbances | Eye gaze direction relative to the head |
| Augmenting device (MEMS) microphones Number of microphones: 12 or more | Sound sources. Reverberation. | Direction of arrival Position of targets Position of microphone Number of sound sources Environment characteristics - reverberation . . . |
| Radio antenna receiver 1 per ear | Electromagnetic waves | RSS RSSI Access point IDs Access point location Position Velocity |
| Radio antenna transmitter 1 per ear | Electromagnetic waves | |
| Magnetic antenna (T-coil) 1 per ear | Magnetic signal representing sound -- a potential disturbance for navigation | magnetic field disturbance informed DOA - the sound in the T-coil can be used to estimate DOAs to targets |
| Bluetooth transmitter 1 per ear | Radio signal | Transmitter position by external network |
| Bluetooth receiver | Radio signal | Position Other information? |
| Ultra sound sensors, 1 per ear | Distance to objects. Object shape, etc. | Distance to objects. Can be used to produce a depth map w.r.t. the sensor. |
| Front camera | Object shape, etc. | Map w.r.t. the sensor |
| Eye camera | Pupil tracking | Eye gaze |

In the following the term 'augmenting device' is used. The augmenting device comprises a number of microphones and may e.g. form part of the hearing device, or be a separate device in communication with the hearing device.

Use Cases for SLAM:

1. One Stationary Listener (User) and N Stationary Sound Sources in a Room (Conference Scenario, Restaurant)

Figure 4:
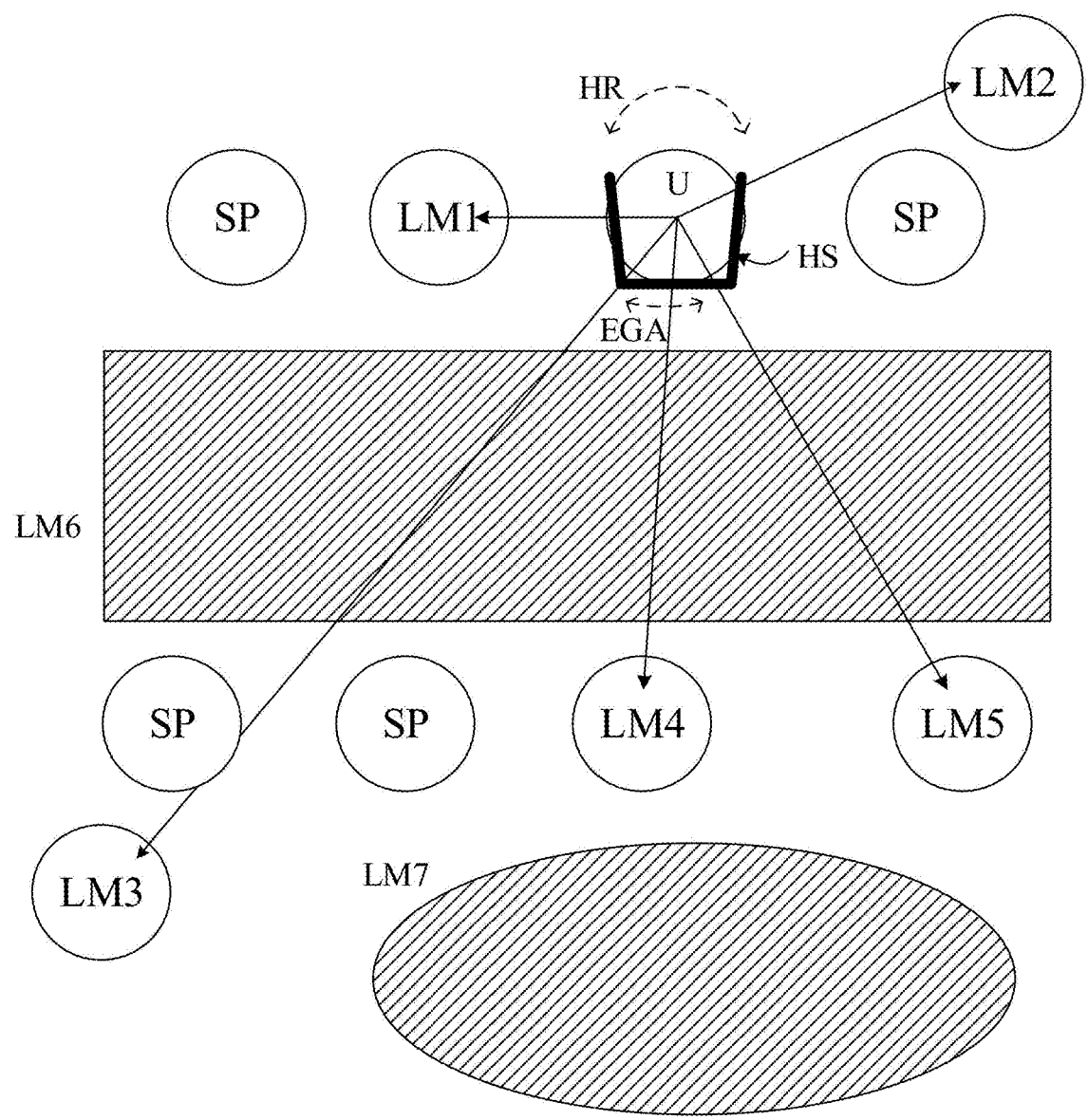
FIG. 4 shows a scenario comprising a multitude of landmarks in the form of number of (simultaneous or intermittent) talkers, a number of silent persons and additional landmarks, and a user wearing a hearing system according to the present disclosure.

FIG. 4 shows a scenario comprising a multitude of landmarks (LMi, i=1, 2, 3, 4, 5) in the form of number of (simultaneous or intermittent) talkers in an environment around a user (U) wearing a hearing system (HS) according to the present disclosure. The environment (e.g. representing a restaurant) further comprises a number of silent persons (SP) and additional landmarks (e.g. objects denoted LM6, LM7, e.g. tables or other environmental structures).

Here a 3D Accelerometer, a 3D Gyroscope, and a 3D Magnetometer, may be used to estimate the head rotation (HR) of the listener (User U). An eye gaze angle (EGA) may e.g. be determined using an eye tracking camera or electrodes for measuring Electroocculography (EOG) potentials.

The Augmenting device (MEMS) microphones are e.g. integrated in a spectacle frame of the hearing system and used in combination to estimate the direction of arrival of the N stationary sound sources, cf. e.g. [Skoglund et al.; 2017].

Using the same microphones on a sensor-integration device, cf. e.g. [Farmani et al.; 2015]

Combing remote microphones and head-worn microphones.

Ultrasound sensors are e.g. used to measure the distance to each N stationary sound sources. A front camera is e.g. used to map the N stationary sound sources.

2. One Stationary Listener and N Mobile Sound Sources in a Room (Event, Like a Theater)

Here the 3D Accelerometer, 3D Gyroscope, and the 3D Magnetometer, are used to estimate the head rotation of the listener.

The Augmenting device (MEMS) microphones are used to in combination to track the direction of arrival of the N mobile sound sources. In an embodiment, the number of (MEMS) microphones is larger than 4, such as 12 or more. In an embodiment, the augmenting device (e.g. the microphones) is used to estimate target velocity through Doppler effect.

The ultrasound sensors are used to measure the distance to each N mobile sound sources. The front camera is used to map the N mobile sound sources.

3. One Mobile Listener and N Mobile Sound Sources in a Room (the Dynamic Cocktail Party)

The 3D Accelerometer, 3D Gyroscope, 3D Magnetometer, Radio Antenna Receiver, Magnetic antenna (T-coil), and Bluetooth receiver are used to track the position of the mobile listener, and the head rotation of the listener.

The augmenting device (MEMS) microphones are used to in combination to track the direction of arrival of the N mobile sound sources. The ultrasound sensors are used to measure the distance to each N mobile sound sources. The front camera is used to map the N mobile sound sources.

4. One Mobile Listener and N Stationary Sound Sources in a Building (an Empty Museum)

The 3D Accelerometer, 3D Gyroscope, 3D Magnetometer, Radio antenna receiver, Magnetic antenna (T-coil), and Bluetooth receiver are used to track the position of the mobile listener, and the head rotation of the listener.

The Augmenting device (MEMS) microphones are used to in combination to track the direction of arrival of the N stationary sound sources.

Radio antenna transmitter and Bluetooth transmitter are used to communicate with beacons. The ultrasound sensors are used to measure the distance to each N mobile sound sources. The front camera is used to map the N mobile sound sources.

5. One Mobile Listener and N Mobile Sound Sources in a Building (Crowded Museum)

The 3D Accelerometer, 3D Gyroscope, 3D Magnetometer, Radio antenna receiver, Magnetic antenna (T-coil), and Bluetooth receiver are used to track the position of the mobile listener, and the head rotation of the listener.

The Augmenting device (MEMS) microphones are used to in combination to track the direction of arrival of the N mobile sound sources Radio antenna transmitter and Bluetooth transmitter are used to communicate with beacons. The ultrasound sensors are used to measure the distance to each N mobile sound sources. The front camera is used to map the N mobile sound sources.

B. Determining the (Sound) Source in User's Focus of Attention for the Moment

Put electrodes (dry electrodes) where skin touches the device, at least two electrodes.
a. Estimate the position and rotation of the head in the physical scene (see above)
b. Estimate the eye-gaze vector relative to the head
i. Combine a and b in the SLAM solutions above.
1. Compensating for the Missing DC Component in EOG.
a. By using "deadreckoning"/modelling/estimation of the eye gaze (position)
b. Relating this to landmarks (we can for this part of SLAM assume that we know the landmarks), and using on-line re-calibration to landmarks or zero gaze angle.
2. Modeling of Different Behaviors when Head-Movements (IMU) and Eye-Movements (EOG) are Integrated into One SLAM Model
a. Fixations. If the estimate classifies that we are in a fixation we have two sources for estimating the eye-position:
i. The EOG signal
ii. The opposite IMU signal. Here the assumption (and the literature) says that when you are fixating the oculomotor system tries to keep a fixated picture on the retina. Therefore, the head-movements are registered in the balance organ (and proprioceptors in the muscle coils in the neck), and directly (through a feedback control system) affect the eye-muscles to contra-movements to compensate for the head-movement. Thus, head-movements and eye-movements are tightly coupled. So in this model (fixation) also the IMU will (also) register the eye-movements with opposite sign.
b. Saccades. Model saccades, that is when the person switch from fixations towards a new target.
c. Smooth pursuit. Model smooth pursuit, that is slow eye-movements (typically following a target at a distance). Difficult to detect with EOG since the change rate is so low (comparable to the DC-drift and thus filtered out), can possibly be traced from the IMUs.
3. Given a Stable and Reliable Eye-Gaze Signal, Look at the Statistics of the Looking Behavior so to Verify the Landmarks and Combine that with the Other Sensors (DOA Estimation).

The use of eye gaze to control a hearing device, e.g. a beamformer is e.g. described in EP3185590A1.

Alternatively, if size and power consumption permits, an eye-camera could be included in the device, which tracks the pupil (REFS, Mobile eye, pupillabs.com). This is e.g. dealt with in EP2813175A2.

C. Augmenting/Enhancing the Source in the User's Focus

Given the SLAM localization and mapping and the estimated eye-gaze direction N beams are calculated from the Augmenting device microphone (MEMS) signals, one beam for each sound source and pointing in the direction of the DOA estimate. E.g. MVDR beamformers. The source that is in the user's focus is defined as where the eye-gaze vector is pointing in the absolute coordinate system.

Furthermore, DNNs or other Noise cancelling techniques (e.g. Virtanen et al. 2017) can be used to further suppress the sources that are not in the user's focus.

Another complementing solution (e.g. together with, or instead of the use of eye gaze) would be to use face recognition and stream segregation in combination with the teaching of the present disclosure (e.g. using standard face recognition algorithms, to place face positions on the map). By using an image sensor, e.g. a frontal camera/scene camera, and by using face recognition algorithms (cf. e.g. http://www.face-rec.org/algorithms/), the position of one or several faces in the image/video can be determined, video-frame by video-frame. The image sensor may be located on the spectacle frame(s), e.g. a cross-bar to provide a frontal field of view relative to the user (cf. e.g. FIG. 1A, 1B, e.g. sensors $S_{13}$, $S_{23}$). Combined with other sensors of the hearing system (e.g. IMU, RSS, acoustic DOA, magnetic field), the position of the face(s) can be determined in the reference coordinate system.

Another complementing solution would be to use source classification based on video and audio. By combining video and audio data, there are several ways to determine the position of human objects in the reference coordinate system, visual by the scene camera with face recognition (cf. above), acoustic by DOA and analysis of speaking objects.

Figure 5A:
FIG. 5A shows an augmenting device comprising a head worn frame supporting a microphone array comprising a multitude of microphones (e.g. (MEMS) microphones)
Figure 5B:
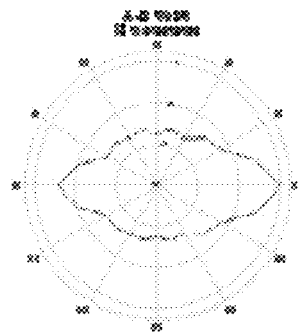
FIG. 5B shows a beamformer with 0 degrees horizontal angle relative the frontal direction.
Figure 5C:
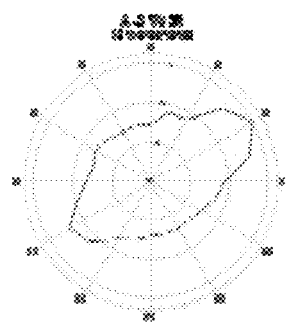
FIG. 5C shows a beamformers with 30 degrees horizontal angle relative the frontal direction.
Figure 5D:
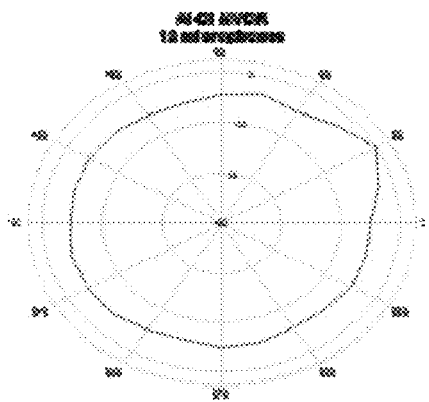
FIG. 5D shows the 30 degrees beamformer of FIG. 5C in severe reverberant conditions.

FIG. 5A shows an augmenting device comprising a head worn frame supporting a microphone array comprising a multitude of microphones (e.g. (MEMS) microphones), FIG. 5B shows a beamformer with 0 degrees horizontal angle relative the frontal direction, FIG. 5C shows a beamformers with 30 degrees horizontal angle relative the frontal direction, and FIG. 5D shows the 30 degrees beamformer of FIG. 5C in severe reverberant conditions.

Use the eye-gaze vector to weigh (weighing function as a function of angle relative to the eye-gaze vector) the relative amplitude of the different beamformers (to make the acoustic object in focus being enhanced, but without completely removing the other acoustic object, a target enhancement of about 12 dB is suggested).

Figure 6:
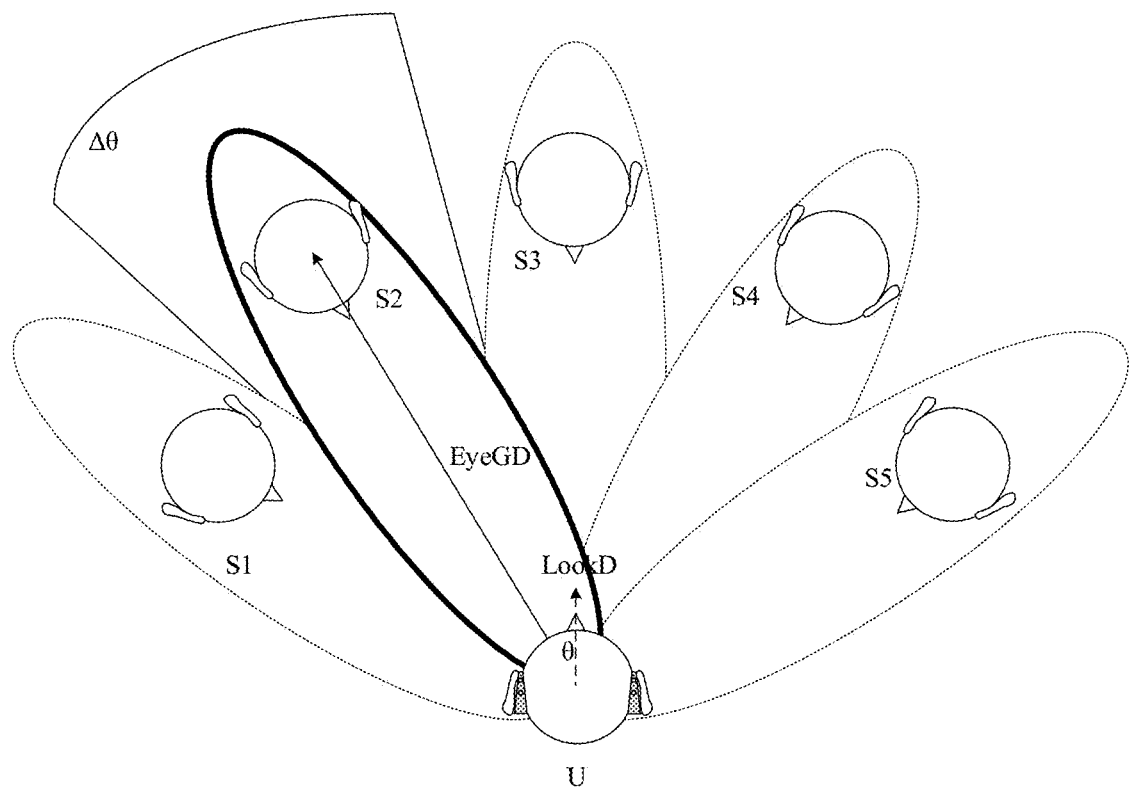
FIG. 6 shows a situation of use EarEOG control of a beamformer of a hearing device according to the present disclosure.

FIG. 6 shows a situation of use EarEOG control of a beamformer of a hearing device according to the present disclosure. Steerable real-time beamformers can implemented in hearing devices. In an embodiment, an EarEOG control signal is used to steer the beamformer angle of maximum sensitivity towards the gaze direction.

The scenario of FIG. 6 is e.g. discussed in EP3185580A1. It illustrates a table situation with quasi constant location of a multitude of occasional talkers/listeners (S1-S5). In an embodiment, the hearing devices of a hearing system according to the present disclosure provides eye gaze control (i.e. comprise electrodes for picking up body potentials and adapted for exchanging amplified voltages based thereon to provide a control signal representative of a current eye gaze direction (EyeGD in FIG. 6) of the user, e.g. relative to a look direction (LookD in FIG. 6) of the user). Each hearing device comprises a beamformer for providing a beam (i.e. the microphone system has a maximum in sensitivity in a specific direction) directed towards a target sound source, here a talker in the vicinity of the user, controlled by a user's eye gaze. For such situation, a beamformer filtering unit for providing a number of beamformers directed at respective localized sound sources in the environment of a user are provided using map data according to the present disclosure. Alternatively, or additionally, predefined look vectors (transfer functions from sound source to microphones, or corresponding relative transfer functions) and/or filter weights corresponding to a particular direction may be determined and stored in a memory unit MEM of the hearing device, so that they can be quickly loaded into the beamformer, when a given talker is selected. Thereby a beamformer directed at a sound source of current interest of the user can be activated via eye gaze control. Thereby the non-active beams can be considered to represent virtual microphones that can be activated one at a time.

FIG. 6 shows an application of a hearing system according to the present disclosure for segregating individual sound sources in a multi-sound source environment. In FIG. 6, the sound sources are persons (that at a given time are talkers or listeners) located around a user (U, that at the time illustrated is a listener). The user (U) wears a hearing system according to the present disclosure that allows segregation of each talker and allows the user to tune in depending on the person (S1, S2, S3, S4, S5) that is currently speaking as indicated by (schematic) elliptic beams of angular width ($\Delta\theta$) sufficiently small to enclose (mainly) one of the persons surrounding the user. In the example of FIG. 6, the person speaking is indicated by S2, and the sound system is focused on this person as indicated by direction θ of eye gaze of the user (EyeGD) and a bold elliptic beam including the speaker (S2).

In an embodiment, the hearing device or devices of the hearing system worn by the user (U) are hearing devices according to the present disclosure. Preferably, the hearing system comprises two hearing devices forming part of a binaural hearing system, e.g. a binaural hearing aid system. In an embodiment, the sensor part of the hearing devices comprises a number of electromagnetic sensors each comprising a sensing electrode configured to be coupled to the surface of the user's head (e.g. at or around an ear or in an ear canal), when the hearing device is operatively mounted on the user. In an embodiment, the sensor part comprises an electrical potential sensor for sensing an electrical potential. In another embodiment, the sensor part comprises a magnetic field sensor for sensing a magnetic field (e.g. generated by a user's body, e.g. originating from neural activity in the user's head, e.g. the brain). In an embodiment, the electrical potential and/or magnetic field sensors are configured to sense electric and/or magnetic brain wave signals, respectively. In an embodiment, the sensing electrode(s) is(are) configured to be capacitively or inductively coupled to the surface of the user's head, when the hearing device is operatively mounted on the user. In an embodiment, the electrical potential sensor comprises a sensing electrode configured to be coupled to the surface of the user's head (e.g. at or around an ear or in an ear canal), when the hearing device is operatively mounted on the user. In an embodiment, the sensing electrode is configured to be directly (e.g. electrically (galvanically)) coupled to the surface of the user's head (e.g. via a 'dry' or 'wet' contact area between the skin of the user and the (electrically conducting) sensing electrode), when the hearing device is operatively mounted on the user.

Another complementing solution would be to use visually based eye-trackers, e.g. glasses with cameras or eye-glasses with EOG (see e.g. Jins Meme, https://jins-meme.com/en/eyewear-apps).

By Kalman-filtering the output from (Ear)EOG sensors (or other eye trackers) the eye-angle (cf. e.g. angle θ in FIG. 6) relative to the head's nose-pointing direction (cf. e.g. LookD in FIG. 6) can be estimated. By Kalman-filtering the output from 9DOF sensors (9 degree of freedom sensors, 3D accelerometer, 3D gyroscope, 3D magnetometer), or other motion-tracking devices—placed at head level close to the ear—the absolute head-angle relative to the local magnetic field and/or local gravity field can be determined. The absolute head-angle relative to the room can be determined in case the local magnetic field and local gravity field is/are is known (e.g. measured by a magnetic field sensor and an accelerometer, respectively) for the room in question. By combining the outputs from the (Ear)EOG and 9DOF another (or the same) Kalman filter can be made whose output is the absolute eye-angle relative to the room.

By further Kalman-filtering (e.g. using another or the same Kalman filter) the output from the absolute eye-angle relative to the room for Simultaneous Location and Mapping (SLAM), a kind of 'hotspot(s)' can be estimated, where some eye-gaze angles are more plausible than others (the person is probably looking more at the persons in the scene than at the backgrounds). The principle idea is to extend the Kalman filter, where eye-gaze angle is a state, with a number of states/parameters that describe the angle to the 'hotspots' (the Map in general robotic-terms). This principle works well if you switch between a number of discrete hotspots as the case is in this application. The Map can be points or normal-distributions, assuming that the eye-gaze angle follow a mix of gauss-distributions.

Extended Kalman filter:

In the extended Kalman filter (EKF), the state transition and observation models don't need to be linear functions of the state but may instead be differentiable functions.

$$x_k = f(x_{k-1}, u_{k-1}) + w_k$$

$$z_k = h(x_k) + v_k$$

where $w_k$ and $v_k$ are the process and observation noises, which are both assumed to be zero mean multivariate Gaussian noises with covariance $Q_k$ and $R_k$ respectively. $u_{k-1}$ is the control vector.

The function $f$ can be used to compute the predicted state from the previous estimate and similarly the function h can be used to compute the predicted measurement from the predicted state. However, $f$ and h cannot be applied to the covariance directly. Instead a matrix of partial derivatives (the Jacobian) is computed.

At each time step, the Jacobian is evaluated with current predicted states. These matrices can be used in the Kalman filter equations. This process essentially linearizes the non-linear function around the current estimate And if we use e.g., particle filter for SLAM, known as FastSLAM, then the functions h( ) and $f$( ) need not even be differentiable.

Including a smartphone (or perhaps several smartphones, e.g. belonging to other users, sound sources (landmarks)) into the loop, their on-board sensors may also be utilized by the hearing system, either alone or in combination with the hearing device (e.g. embodied in glasses and/or hearing aids). In an embodiment, the smartphone may be used to compute a direction of arrival (DOA) of a sound source, e.g. in a restaurant scenario, cf. e.g. FIG. 6, e.g. in combination with the hearing device(s) as (which provides more microphones, e.g. microphone pairs). The relative position and orientation between the user and the hearing device can be calculated e.g., via IMU, smartphone-device, DOA, or other methods. It can also be used as a remote microphone (array), possibly improving beamforming and such.

Figure 7:
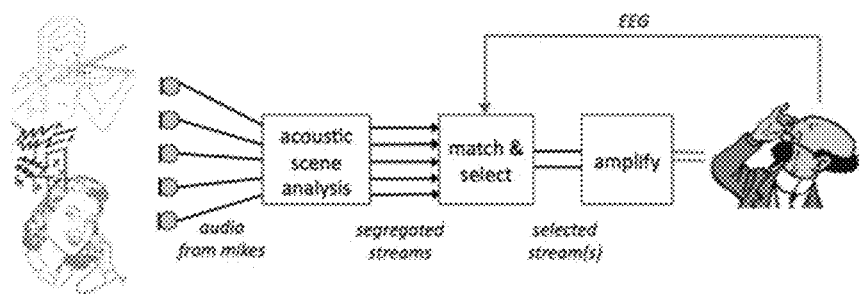
FIG. 7 shows a situation of use EarEEG control of a beamformer of a hearing device according to the present disclosure.

FIG. 7 shows a situation of a use of EarEEG control of a beamformer of a hearing device according to the present disclosure. FIG. 7 illustrates a situation where the control unit configured to allow a user to select one of the localized sound sources as a sound source of current interest comprises a user interface based on detection of brain waves using electrodes for picking up EEG potentials from the user's brain. At least some of the electrodes may be located in or on the hearing device. The different localized sound sources may be identified as proposed by the present disclosure (e.g. using a SLAM algorithm) and e.g. sequentially (or simultaneously) presented to the user by directing beamformers at the sound sources and let the user choose the sound source of current interest via a comparison of recorded EEG signals with the individual sound signals e.g. extracted by the beamformers. An example of such brain-wave dependent audio processing is e.g. presented in US20140098981A1.

Figure 8A:
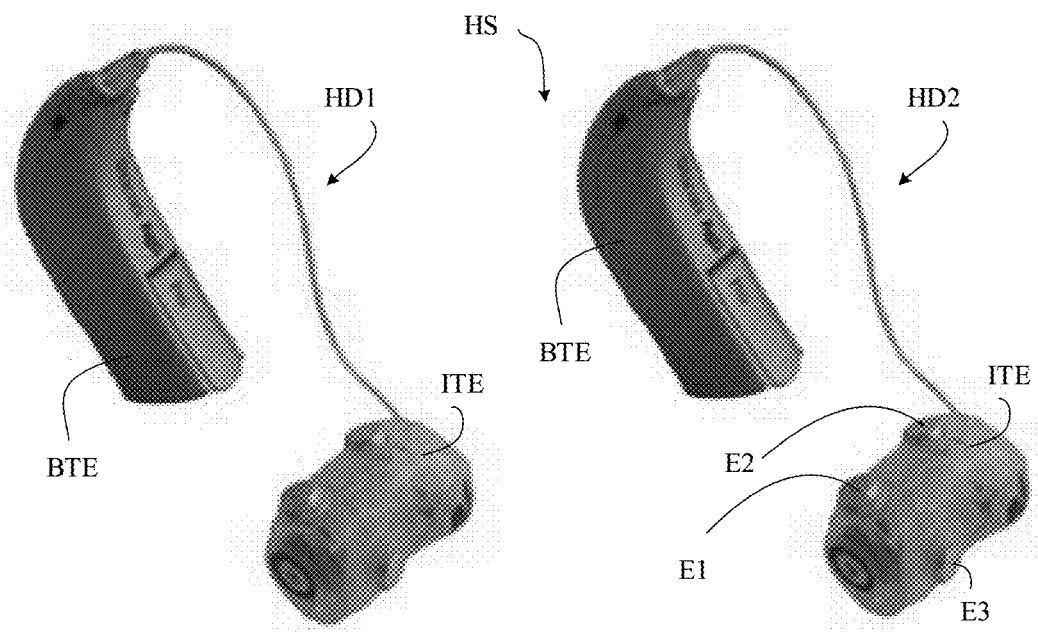
FIG. 8A shows a pair of behind the ear (BTE) hearing devices comprising electrodes on a mould surface of an ITE part.

FIG. 8A shows a pair of behind the ear (BTE) hearing devices comprising electrodes on a mould surface of an ITE part. The embodiment of FIG. 8A shows electrodes (E1, E2, E3) located on the surface of (customized) in-the-ear moulds (ITE) of a hearing system (HS) comprising first and second hearing devices (HD1, HD2), but may also be applied to more general purpose domes or ITE-parts, or may be integrated in a behind the ear part (BTE). In an embodiment, the electrodes are 'conventional (dry or wet) electrodes' for establishing a direct electric contact between skin and electrode.

Figure 8B:
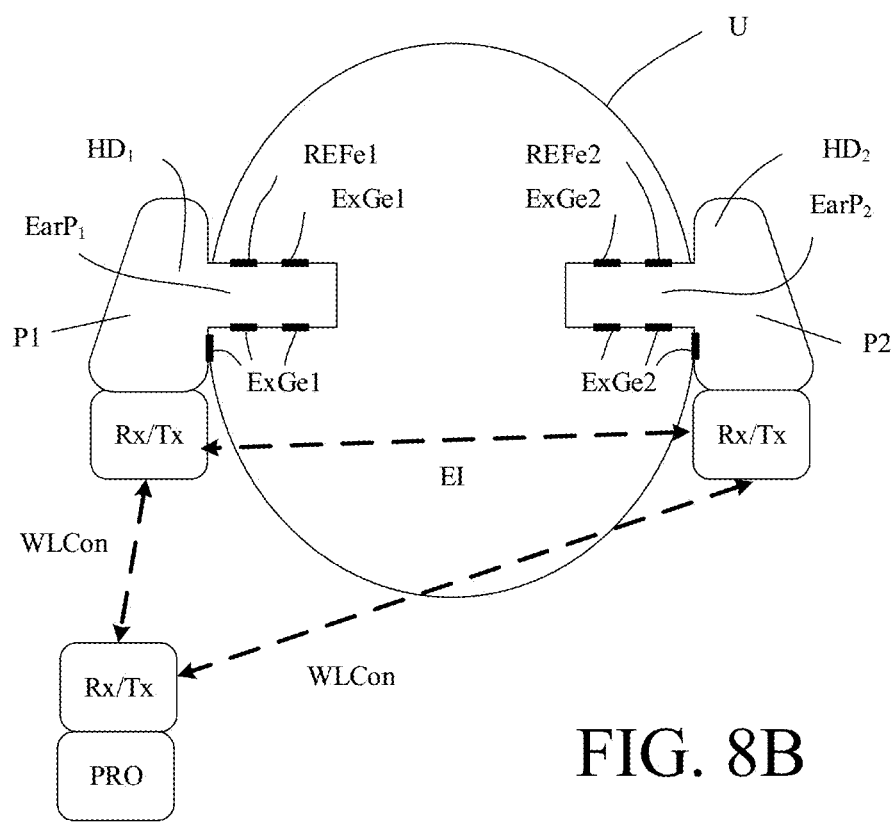
FIG. 8B shows a pair of hearing devices comprising electrodes in an ear canal as well as outside the ear canal of the user, and a wireless interface for communicating with a separate processing part.

FIG. 8B shows a pair of hearing devices comprising electrodes in an ear canal as well as outside the ear canal of the user, and a wireless interface for communicating with a separate processing part. In the embodiment of FIG. 8B, the first and second hearing devices (HD$_1$, HD2) comprises first and second parts (P1, P2), respectively, each being located partially in an ear canal and partially outside the ear canal of the user (e.g. in concha or pinna or behind the ear). Further, the first hearing devices (HD$_1$, HD$_2$) each comprises EEG- or EOG-electrodes, or a mixture thereof (ExGe1, ExGe2), and a reference electrode (REFe1, REFe2), respectively, arranged on the outer surface of the respective ear pieces (EarP1, EarP2). Each of the first and second parts (P1, P2) comprises a number of EEG- and/or EOG-electrodes (ExGe1, ExGe2), here four are shown (but more or less may be present in practice depending on the application), and a reference electrode (REFe1, REFe2). Thereby a reference voltage ($V_{REF2}$) picked up by the reference electrode (REFe2) of the second part (P2) can be used as a reference voltage for the EEG- or EOG-potentials ($V_{ExG1i}$) picked up by the EEG- or EOG-electrodes (ExGe1) of the first part (P1), and vice versa. In an embodiment, the first and second hearing devices (HD$_1$, HD$_2$) implements a binaural hearing system, e.g. a binaural hearing aid system. The reference voltages ($V_{REF1}$, $V_{REF2}$) may be transmitted from one part to the other (P1<->P2) via electric interface EI (e.g. a wired or wireless connection, and optionally to or via auxiliary device PRO, cf. wired or wireless links WLCon). The two sets of EEG-signal voltage differences ($\Delta V_{ExG1}$, $\Delta V_{ExG2}$) can be used separately in each of the respective first and second hearing devices (HD$_1$, HD$_2$) (e.g. to control processing of an input audio signal, or to select one of a multitude of audio sources) or combined in one of the hearing devices and/or in the auxiliary device (PRO, e.g. for display and/or further processing).

Figure 8C:
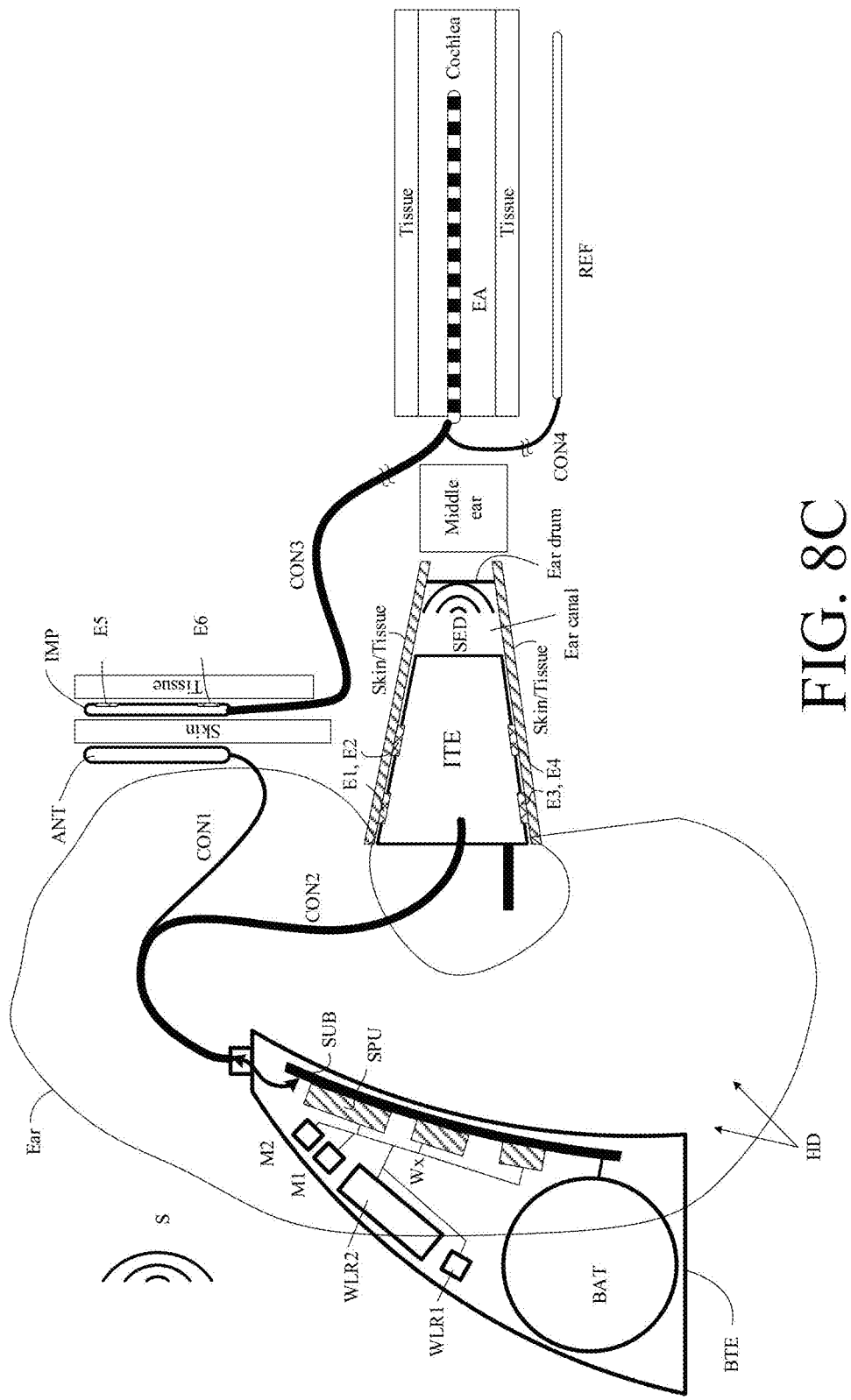
FIG. 8C shows a hearing system comprising a bimodal hearing system comprising an air conduction hearing device as well as a cochlear implant hearing device.

FIG. 8C shows a hearing system comprising a bimodal hearing system comprising an air conduction hearing device as well as a cochlear implant hearing device. FIG. 8C shows an embodiment of a hybrid (bimodal) hearing device (HD) according to the present disclosure comprising an external part (ITE) for acoustically stimulating an ear of a user and an implanted part (IMP) for electrically stimulating the auditory nerve of the (same) ear of the user. The hybrid hearing device comprises a part (ITE) adapted to be inserted into an ear canal of the user to allow acoustic stimulation of the ear drum (Ear drum) from a loudspeaker located in the ITE-part, or in another part of the hearing device in acoustic communication with the ITE-part (e.g. via a tube). The implanted part (IMP) is adapted for being implanted in the head of the user. The hearing device (HD) further comprises a BTE-part adapted for being located at the ear (Ear), e.g. behind the ear (BTE), and a further external part (ANT) electrically connected to the BTE-part via a connecting element CON1. The further external part (ANT) comprises antenna (e.g. an inductor coil) and transceiver circuitry for providing communication between the BTE-part (BTE) and the implanted part (IMP) through the skin (Skin) of the user. The BTE-part is further electrically connected to the ITE-part via a connecting element CON2. The implanted part (IMP) comprises antenna (e.g. an inductor coil) and transceiver circuitry allowing a wireless link to be established between the further external part (ANT) and the implanted part (IMP). The implanted part (IMP) is located under the skin of the user appropriately arranged relative to the further external part (ANT) to allow exchange of data between the two parts and to allow energy from the external part to the implanted part to be transferred. The ITE-part (ITE) and the implanted part (IMP) both comprise electrodes (E1, E2, E3, E4, E5, E6) for picking up (e.g. evoked) potentials (e.g. from the brain) or EOG potentials from the eyes of the user via electrical contact to skin and/or tissue (Skin/Tissue) at the ear or in the ear canal (electrodes E1, E2, E3, E4) of the user and to the skin and/or skull-tissue (Tissue) under the skin (electrodes E5, E6) of the user, respectively. The implanted part comprises an electrode array (EA) and a reference electrode (REF) electrically connected to the implanted part (IMP) via electrical connections CON3 and CON4, respectively (e.g. electrical conductors). The reference electrode (REF) is preferably separated from the electrode array (EA)

by tissue (Tissue), e.g. in that the electrode array is inserted in cochlea (Cochlea) and the reference electrode is positioned outside cochlea.

In the embodiment of FIG. 8C, the ITE-part comprises an electro-acoustic transducer (e.g. a loudspeaker) for acoustically stimulating a first (e.g. lower) frequency range via sound SED played in the residual volume in front of the ear drum and thereby conveyed to the ear drum and further to cochlea via the middle ear (Middle ear).

In the embodiment of FIG. 8C, the implanted part comprises an electrode array (EA) for electrically stimulating a second (higher) frequency range via separate electric stimuli supplied to at least some of the electrodes of the electrode array when located at the auditory nerve, e.g. in cochlea (Cochlea).

The hybrid hearing aid (HD) of FIG. 8C comprises a receiver in the ear (RITE) type hearing aid and a cochlear implant (CI) type hearing aid. The BTE-part (BTE) adapted for being located behind pinna services the ITE-part as well as the implanted part (IMP) via electrical connections CON2 and CON1, respectively. The BTE part (BTE) comprises two input transducers (here microphones) (M1, M2) each for providing an electric input audio signal representative of an input sound signal from a sound source (S) in the environment of the hearing device. The BTE-part further comprises two wireless receivers (WLR1, WLR2) for providing respective directly received auxiliary audio and/or information signals to/from other devices. The BTE-part (BTE) further comprises a substrate (SUB) whereon a number of electronic components are mounted, functionally partitioned according to the application in question (analogue, digital, passive components, etc.), but including a configurable signal processing unit (SPU), coupled to each other and to input and output units via electrical conductors Wx. The configurable signal processing unit (SPU) is adapted to provide separate first and second enhanced signals to the ITE-part and to the implanted part (IMP) allowing a separate (simultaneous) acoustic and electric stimulation, respectively, at an ear of the user. The ITE part (ITE) comprises an output unit in the form of a loudspeaker (receiver) for converting the first enhanced signal from the BTE-unit to an acoustic signal comprising frequencies in a first frequency range (providing, or contributing to, acoustic signal SED at the ear drum (Ear drum)). The implanted part (IMP) is configured to generate or convey electric stimuli representative of a second frequency range based on the second enhanced signal from the BTE-unit to the electrode array (EA).

The BTE-part (BTE) further comprises a battery (BAT) for energizing electronic components of the hearing aid (e.g. including electronic components of the ITE-part, the ANT-unit and the implanted part (IMP)).

D. Calculating the Auditory Display (Sound to be Presented to the Left and Right Ears) of the Enhanced Sound Scene and Transmitting this to a Pair of Hearing Aids.

a. Calculate auditory display for acoustic output i. Calculate left and right ear head-related transfer functions (HRTFs) for each N acoustic objects. E.g. HRTF according to the CIPIC data base.

ii. Calculate the augmented auditory display by (for each ear) summing the N acoustic object with the above weighting function, e.g. based on eye-gaze or face recognition, etc.

b. Transmit the left and right output to the receiver for the corresponding ear i. Via electrical cables ii. Via wireless communication (e.g. from the sensor-integration device to the hearing instrument) to avoid cables [e.g. BLE, NFR, telecoil]

Figure 9A:
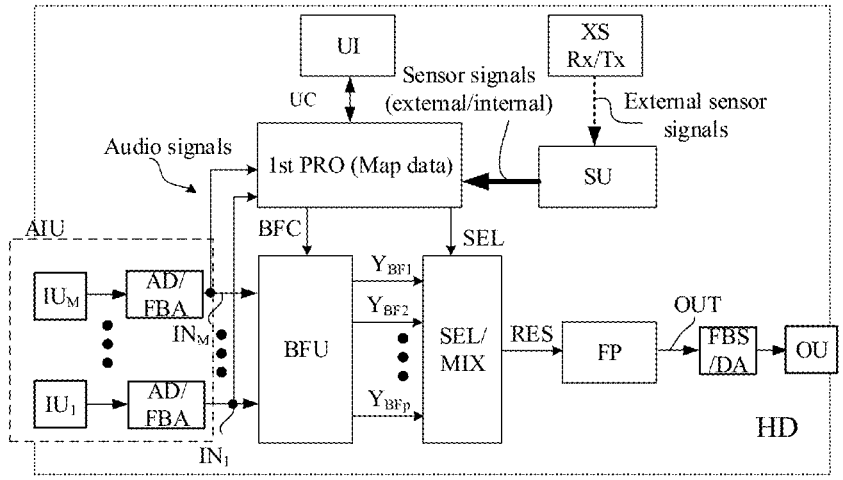
FIG. 9A shows a first embodiment of a hearing device according to the present disclosure.

FIG. 9A shows an embodiment of a hearing system comprising a hearing device according to the present disclosure, The hearing system comprises a hearing device (HD), e.g. a hearing aid, adapted to be worn by a user and configured to generate and update over time data representative of a map of a current environment of the user. The hearing device is configured to localize the user relative to one or more sound sources in the environment of the user in interaction with the map data. The hearing system comprises receiver circuitry for receiving signals from multitude of signal sources (AIU) and/or from one or more sensors (XS Rx/Tx, SU). The receiver circuitry provides corresponding electric input signals. The multitude of signal sources comprises a number N of localized sound sources (audio signals, sensor signals). The receiver circuitry may e.g. comprise a multitude M of microphones configured to be stationary relative to the user, each microphone being adapted to pick up sound from sound sources in the environment and for providing an electric input sound signal ($IN_1, \ldots, IN_M$) comprising the sound. The audio input unit (AIU) comprises M input units ($IU_1, \ldots, IU_M$), e.g. comprising M input transducers, e.g. microphones or a mixture of input transducers and wireless audio receivers, and a corresponding number of analogue to digital converters and analysis filter bank, as appropriate to provide the electric input sound signal ($IN_1, \ldots, IN_M$) (Audio signals) in a time-frequency representation (as a number of time variant frequency sub-band signals).

The hearing system (HD) further comprises a first processor ($1^{st}$ PRO (Map data)) for, preferably continuously, estimating localization data relative to the user of the number N of, stationary or mobile, localized sound sources in the environment, such localization data for a given sound source e.g. comprising a direction of arrival of sound and/or a distance from said given sound source to the user, based on the multitude of electric input sound signals from the microphone array, and optionally, additionally, on sensor signals from the one or more sensors (and/or inputs UC from a user interface, UI).

The first processor ($1^{st}$ PRO) is configured to (continuously, e.g. with a specific frequency/repetition rate) processing said electric input signals (audio signals and sensor signal) and providing data representative of an approximate, time dependent map of said confined environment comprising a present location of said number of, stationary or mobile, landmarks, including the N localized sound sources, and an estimate of a present location of the user relative to the number of landmarks in the confined environment. The first processor ($1^{st}$ PRO) may e.g. produce aid map data using a SLAM algorithm.

The sensor unit (SU) may comprise a number of internal sensors and provide a number of corresponding internal sensor signals. Hearing device (HD) may further or alternatively comprise a number of receivers (XS, Rx/Tx, e.g. wireless receivers) for receiving signals from external sensors (e.g. sensors from a smartphone or signals from an FM-transmitter, etc.) and providing corresponding External sensor signals, to the sensor unit (SU). The sensor unit (SU) is configured to forwarding the internal and external sensor signals to the first processor ($1^{st}$ PRO), cf. bold arrow denoted Sensor signals (external/internal).

The first processor (1$^{st}$ PRO) is configured to, preferably continuously, estimating one or more preferred sound sources that is of current interest to the user among the sound sources presently in the user's environment (e.g. fully or partially based on a control signal UC from a user interface (UI)). A resulting audio signal RES comprising said sound source (or weighted mixture of sound sources) of current interest to the user is provided by selector/mixer (SEL/MIX) based on the current p beamformed signals $Y_{BF1}$, $Y_{BF2}$, ..., $Y_{BFp}$ (cf. e.g. beams FIG. 6 directed at sound sources of current interest S1-S5) from the beamformer filtering unit (BFU) and control signal SEL (e.g. based on or influenced by inputs (UC) from the user interface (UI)).

The hearing system further (optionally) comprises a further processor (FP) for enhancing the preferred sound source(s) RES among said N sound sources and providing a processed electric output signal OUT. The processed electric output signal OUT is fed to an output unit (OU) (via synthesis filter bank (FBS) and digital to analogue conversion (DA) circuitry, as appropriate). The output unit provides stimuli perceivable to the user as sound (cf. 'Sound stimuli-out' in FIG. 9B).

Figure 9B:
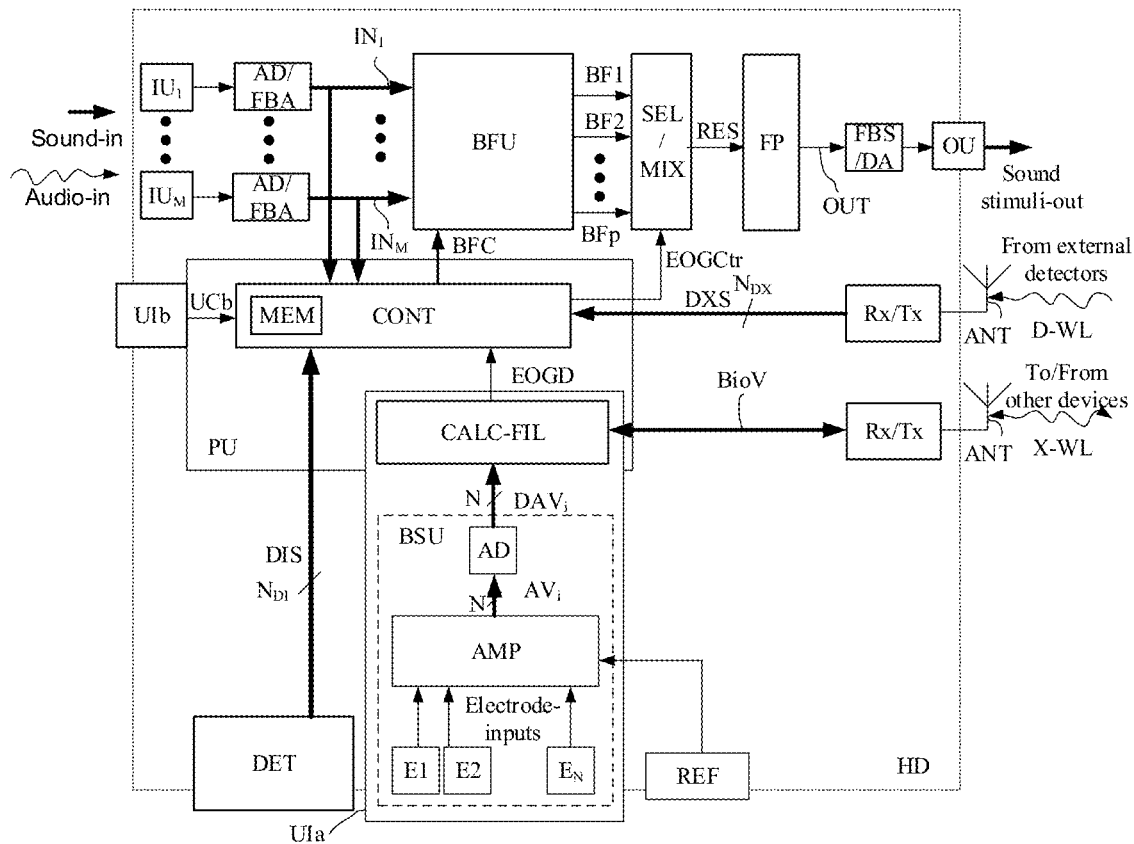
FIG. 9B shows a second embodiment of a hearing device according to the present disclosure.

FIG. 9B illustrates a second embodiment of a hearing device (HD) according to the present disclosure. The embodiment of FIG. 9B comprises the same functional elements as the embodiment of FIG. 9A. The hearing device, e.g. a hearing aid, (HD) comprises a forward path from a number M of input units ($IU_1$, ..., $IU_M$) for picking up sound or receiving electric signals representing sound ('Sound-in', 'Audio-in', respectively in FIG. 9B) to an output unit (OU) for providing stimuli ('Sound stimuli-out') representing said sound and perceivable as sound by a user wearing the hearing device. The forward path further comprises a number M of analogue to digital converters (AD) and analysis filter banks (FBA) operationally coupled to each their input unit ($IU_1$, ..., $IU_M$), where necessary, and providing respective digitized electric input signals $IN_1$, ..., $IN_M$ in time-frequency representation, each comprising a number K of frequency sub-band signals $IN_1(k,m)$, ..., $IN_M(k,m)$, k and m being frequency and time indices, respectively, k=1, ..., K. The forward path further comprises a beamformer filtering unit (BFU), or weighting unit, receiving the electric input signals $IN_1$, ... $IN_M$ as inputs and providing a resulting beamformed signals BF1, ..., BFp (where p is number of beamformers provided by the hearing device), each providing a weighted combination of the M electric input signals. In other words, $BFx = IN_1(k,m)^*w_{1x}(k,m), ..., IN_M(k,m)^*w_{Mx}(k,m)$, where $w_{ix}$, i=1, ..., M, are real or complex (in general, time and frequency dependent) weights for a given beamformer BFx (x=1, p). The forward path further comprises a selector/mixer (SEL/MIX) for selecting the signal or combination of signals RES of current interest to the user. The selector (SEL) is controlled by the eye gaze control signal EOGCtr from the control unit (CONT). The forward path further comprises a signal processor (FP) for further processing the resulting signal RES, and providing a processed signal OUT. The signal processor (FP) is e.g. configured to apply a level and/or frequency dependent gain or attenuation according to a user's needs (e.g. hearing impairment), and/or to otherwise enhance the signal (RES). The forward path further comprises a synthesis filter bank (FBS) for converting frequency sub-band signals OUT to a single time-domain signal, and optionally a digital to analogue conversion unit (DA) to convert the digital processed time-domain signal to an analogue electric output signal to the output unit (OU).

The hearing device (HD) further comprises a bio signal unit (BSU) for picking up bio signals from the user's body. The bio signal unit (BSU) comprises a sensor part ($E_1, E_2, ..., E_N$), adapted for being located at or in an ear and/or for fully or partially being implanted in the head of a user. The sensor part comprises an electrical potential sensor for sensing an electrical potential from the body of the user, in particular from the head, e.g. due to brain activity or eye movement. In FIG. 9B, the sensor part is embodied as electrodes $E_1, E_2, ..., E_N$, which are electrodes of the hearing device configured to contact skin or tissue of the user's head (cf. e.g. FIG. 8A, 8B or 8C), when the hearing device is operationally mounted on the user (e.g. in an ear canal) or implanted in the head of the user. The bio signal unit (BSU) further comprises an amplifier (AMP), in the form of electronic circuitry coupled to the electrical potential sensor part to provide an amplified output. The amplifier, e.g. a differential amplifier, receives a number of potentials $P_1, P_2, ..., P_N$ from the electrodes $E_1, E_2, ..., E_N$, and a reference potential $P_0$ from a reference electrode (REF), and provides respective amplified voltages $AV_1, AV_2, ..., AV_N$. The amplified voltages are fed to respective analogue to digital converters (AD) providing digitized amplified voltages $DAV_i$ (i=1, 0.2 ..., N). In an embodiment, the amplifier (AMP) includes analogue to digital conversion or is constituted by analogue to digital converters.

In an embodiment, at least one (such as all) of the input units comprises an input transducer, e.g. a microphone, for converting sound (Sound-in) to electric signals representing the sound. In an embodiment, at least one (such as all) of the input units comprises a wireless transceiver, e.g. a wireless receiver, e.g. configured to receive a signal (Audio-in) representative of sound picked up by a remote (wireless) microphone.

The hearing device further comprises a detector unit (DET) comprising a number $N_{DI}$ of detectors for providing sensor data (signals DIS) representative of a current location of the user and/or of landmarks in the user's environment, e.g. representative of the user's head, in a fixed coordinate system (e.g. relative to a specific location, e.g. a room), or in movable coordinate system following the user. In an embodiment, the location sensor comprises a head tracker. In an embodiment, the location sensor comprises an accelerometer and a gyroscope. In an embodiment, the location sensor comprises a 9 degree of freedom sensor, comprising a 3D accelerometer, a 3D gyroscope, and a 3D magnetometer. The detector signals DIS are fed to the control unit (CONT) for comparison and processing, e.g. to provide or update the map data.

The hearing device (HD) is configured to receive sensor signals from external sensors, e.g. regarding properties of the local environment, and/or from electromagnetic transmitters, e.g. FM-transmitters, Bluetooth transmitters, etc., e.g. via a wireless link (D-WL) and corresponding antenna and transceiver circuitry or radio receiver(s) (ANT Rx/Tx). In the hearing device (HD), these 'external sensor signals' are denoted DXS (e.g. representing a number NDX of sensors) and fed to control unit (CONT) and used together with the detector signals DIS from the internal sensors to contribute to the generation of update of the map data.

The hearing device further comprises a wireless transceiver (Rx/Tx) and appropriate antenna circuitry allowing reception of bio signals BioV from and transmission of bio signals BioV to another device, e.g. a contra lateral hearing device, e.g. amplified voltages $AV_1, AV_2, ..., AV_N$, e.g. representing eye movement, via a wireless link (X-WL), cf. waved, arrowed line denoted 'To/From other devices' in FIG. 9B. The bio signals BioV from a contra-lateral hearing device are fed to calculation unit (CALC) and compared to the corresponding locally generated bio signal(s) $DAV_i$ (e.g. amplified voltages $V_1, V_2, \ldots, V_N$). In an embodiment, the EarEOG signal is a function (f) of a difference between the left and right amplified voltages $AV_{left}$ and $AV_{right}$, EarEOG=$f(AV_{left}-AV_{right})$. In an embodiment, each pair of voltages, $AV_{1,left}$ and $AV_{1,right}, \ldots, AV_{N,left}$ and $AV_{N,right}$, may provide corresponding ear EOG signals, e.g. EarEOG$_1$=$f(AV_{1,left}-AV_{1,right}), \ldots,$ EarEOG$_1$=$f(AV_{N,left}-AV_{N,right})$. In an embodiment, a resulting ear EOG signal at a given time may be found as an average (e.g. a weighted average; e.g. in dependence of the distance of the electrodes in question from the eyes) of the N ear EOG signals.

The bio signal unit (BSU) and the calculation/filtering unit (CALC-FIL) form part of a user interface UIa. The hearing device or system may comprise a further user interface UIb in communication with the control unit (CONT) and e.g. allowing a user to influence the selection of one or more sound sources of current interest to the user (e.g. their mutual weight, if more than one sound source is of interest to the user at a given time), e.g. via an APP of a remote control device, e.g. a smartphone.

The hearing device further comprises a processing unit (PU), equivalent to the $1^{st}$ processor ($1^{st}$ PRO) of FIG. 9A, for providing a control signal for controlling a function of the hearing device based on the EarEOG signal(s), e.g., controlling the beamformer filtering unit (BFU), e.g. selecting one of a number of predefined beamformers in dependence of an eye gaze control signal EOGCtr (here in selector (SEL)). The predefined beamformers (BF1, BF2, ..., BFp) may e.g. be stored in a memory of the hearing device (e.g. in the control unit CONT), cf. memory MEM), e.g. as sets of beamformer filtering coefficients, each corresponding to a given one of a number of predefined locations of a sound source of interest. The beamformers (and thus the sets of beamformer filtering coefficients or weights) are preferably updated using map data as proposed in the present disclosure. The processing unit (PU) comprises a calculation unit (CALC) configured to combine the sensor data DIS and DXS with the digitized amplified voltages $DAV_i$ (i=1, 0.2 ..., N), representative of (ear) EEG and/or (ear) EOG signals, from the (local) bio signal unit (BSU) and received from a bio signal unit (BSU) of another device, e.g. a contra-lateral hearing device (cf. e.g. wireless link X-WL in FIG. 9B), to provide combined map data and resulting locations of the landmarks (current audio sources and the user). The processing unit (PU) may further comprise a Kalman filter (FIL) (or one or more Kalman filters) for filtering the location data and providing eye gaze angles in a fixed or relative coordinate system, cf. EOG data signal EOGD. The EOG data signal EOGD is forwarded to control unit CONT. Control unit (CONT) provides control signal EOGCtr to the selector (SEL) based on the EOG data signal EOGD. The control unit is further configured to determine updated beamformers (e.g. beamformer filtering coefficients) directed at the current location of sound sources relative to the user (in dependence of map data).

In the embodiment of FIG. 9A or 9B, at least some of the input units ($IU_1, \ldots, IU_M$) may be implemented as microphones ($IT_1, \ldots, IT_M$). The output unit (OU) may e.g. be embodied in one or more of a loudspeaker, a vibrator for a bone-conducting hearing aid, and an electrode array of a cochlear implant hearing aid.

Figure 10:
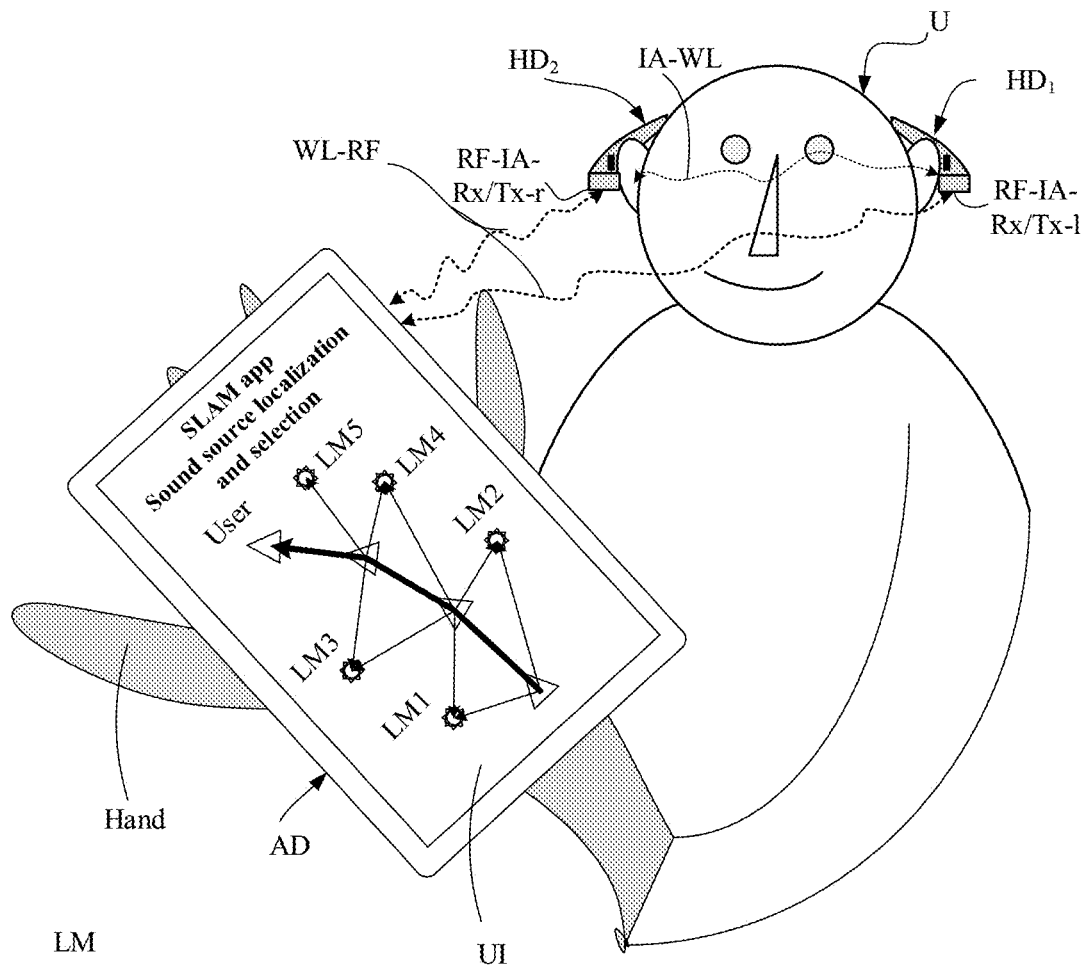
FIG. 10 illustrates a user interface for a hearing system according to the present disclosure.

FIG. 10 illustrates a user interface for a hearing system according to the present disclosure. FIG. 10 shows an embodiment of a hearing system implementing a binaural hearing system comprising left and right hearing devices ($HD_1$, $HD_2$) (e.g. hearing aids) in communication with an auxiliary device (AD), e.g. a cellphone, the auxiliary device comprising a user interface (UI) for the system, e.g. for viewing (and possibly influencing the selection of sound sources of current interest to the user among) the current sound sources ($S_S$) in the environment of the binaural hearing system.

The left and right hearing devices ($HD_1$, $HD_2$) are e.g. implemented as described in connection with FIG. 9A or 9B. The left and right hearing devices ($HD_1$, $HD_2$) and the auxiliary device (AD) each comprise relevant antenna and transceiver circuitry for establishing wireless communication links between the hearing devices (link IA-WL) as well as between at least one of or each of the hearing devices and the auxiliary device (link WL-RF). The antenna and transceiver circuitry in each of the left and right hearing devices necessary for establishing the two links is denoted RF-IA-RX/Tx-1, and RF-IA-RX/Tx-r, respectively, in FIG. 10. In an embodiment, the interaural link IA-WL is based on near-field communication (e.g. on inductive coupling), but may alternatively be based on radiated fields (e.g. according to the Bluetooth standard, and/or be based on audio transmission utilizing the Bluetooth Low Energy standard). In an embodiment, the link WL-RF between the auxiliary device and the hearing devices is based on radiated fields (e.g. according to the Bluetooth standard, and/or based on audio transmission utilizing the Bluetooth Low Energy standard), but may alternatively be based on near-field communication (e.g. on inductive coupling). The bandwidth of the links (IA-WL, WL-RF) is preferably adapted to allow sound source signals (or at least parts thereof, e.g. selected frequency bands and/or time segments) and/or localization parameters identifying a current location of a sound source (or other landmarks, and/or map data) to be transferred between the devices (e.g. to/from the auxiliary device). In an embodiment, processing of the system (e.g. sound source separation) and/or the function of a remote control is fully or partially implemented in the auxiliary device AD (e.g. a smartphone). In an embodiment, the user interface UI is implemented by the smartphone possibly running an APP (termed the 'SLAM app' for 'Sound source localization and selection') allowing to control the functionality of the audio processing device via the smartphone, e.g. utilizing a display of the smartphone to implement a graphical interface (e.g. combined with text entry options).

In an embodiment, the binaural hearing system is configured to allow a user to view a location of sound sources in the environment relative to the user (as e.g. shown in FIG. 2) via the user interface (UI) of the smartphone (which is convenient for viewing and interaction via a touch sensitive display, when the smartphone is held in a hand (Hand) of the user (U)). The sound sources LM1-LM5 displayed by the user interface (UI) are determined according to the present disclosure based on map data, e.g. using a SLAM algorithm. In the illustrated example in FIG. 10, the locality of 5 sound sources LM1, LM2, LM3, LM4 and LM5. In the example of FIG. 10, the user's movement over time relative to the sound sources are illustrated, and the user interface UI is configured to allow the user to indicate which one (or more) of the shown sound sources that are of a current interest (e.g. by clicking on the sound source symbol in question, and possibly indicating a weight of each source if more than one is selected). The binaural hearing system (including the auxiliary device) is configured to transmit information about the selected sound source(s) (and possibly their mutual relative weight) to the left and right hearing devices ($HD_1$, HD$_2$) to allow them to focus the processed output signals presented to the left and right ears of the user on the selected sound sources.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

EP3185590A1 (Oticon) 28 Jun. 2017

[Skoglund et al.; 2017] European patent application number 17179464.7 filed with the European Patent Office on 4 of Jul. 2017 and having the title Direction Of Arrival Estimation In Miniature Devices Using A Sound Sensor Array.

[Farmani et al.; 2015] Mojtaba Farmani; Michael Syskind Pedersen; Zheng-Hua Tan; Jesper Jensen, Informed TDoA-based direction of arrival estimation for hearing aid applications, IEEE 2015 Global Conference on Signal and Information Processing (GLOBALSIP), p. 953-957

EP2813175A2 (Oticon) 17 Dec. 2014

US20140098981A1 (Oticon) 10 Apr. 2014

[Davison; 2003], A. J. Davison. Real-time simultaneous localisation and mapping with a single camera. In Proceedings of the 9th IEEE International Conference on computer vision, pages 1403-1410, Nice, France, 13-16 Oct. 2003.

[Pax et al.; 2008] L. M. Paz, P. Pinies, J. D. Tardós and J. Neira, "Large-Scale 6-DOF SLAM With Stereo-in-Hand," in IEEE Transactions on Robotics, vol. 24, no. 5, pp. 946-957, October 2008.

[Lupton & Sukkarieh; 2008] T. Lupton and S. Sukkarieh. "Removing scale biases and ambiguity from 6DoF monocular SLAM using inertial". In Proceedings of the International Conference on Robotics and Automation (ICRA), pages 3698-3703, Pasadena, Calif., USA, 2008. IEEE.

[Lorenz & Boyd; 2005] Robert G. Lorenz, and Stephen P. Boyd, Robust Minimum Variance Beamforming, IEEE Transactions on Signal Processing, Vol. 53, No. 5, May 2005.

[Richardson & Spivey; 2004] Richardson D C, Spivey M J. "Eye tracking: Research areas and applications". In: Wnek G E, Bowlin G L, editors. Encyclopedia of Biomaterials and Biomedical Engineering. London, UK: Taylor & Francis; 2004. pp. 573-582.

The invention claimed is:

1. A hearing system comprising a hearing device, the hearing device being adapted for being worn by a user, the hearing system comprising
  an audio input unit configured to receive a multitude of audio signals comprising sound from a number of localized sound sources in an environment around the user, and
  a sensor unit configured to receive and/or provide sensor signals from one or more sensors, said one or more sensors being located in said environment and/or form part of said hearing system, and
  a first processor configured to generate and update over time data representative of a map of said environment of the user, said data being termed map data, said environment comprising a number of, stationary or mobile, landmarks, said landmarks comprising said number of localized sound sources, and said map data being representative of the physical location of said landmarks in the environment relative to the user,
wherein the hearing system is configured to,
  generate and update over time said map data based on said audio signals and said sensor signals, and
wherein the hearing device comprises
  a beamformer filtering unit coupled to the audio input unit and configured to provide one or more beamformers based on said multitude of audio signals, and wherein the first processor is configured to control and update over time the beamformer filtering unit in dependence of the map data, and to direct the one or more beamformers towards one or more of the localized sound sources in the environment of the user,
  a signal processor for enhancing said multitude of audio signals and providing a processed electric output signal comprising one or more of the localized sound sources based on the one or more beamformers, and
  an output unit for providing stimuli perceivable as sound to the user based on said processed electric output signal representing or comprising sound from said one or more of said localized sound sources.

2. A hearing system according to claim 1 wherein said beamformer filtering unit comprises a linearly constrained minimum variance (LCMV) beamformer.

3. A hearing system according to claim 1 wherein said first processor is configured to allow a user to select at least one of said localized sound sources as a sound source of current interest.

4. A hearing system according to claim 1 configured to automatically direct said beamformers towards said localized sound sources based on said map data.

5. A hearing system according to claim 1 comprising a memory and being configured to store said map data in said memory, allowing to track the movement of said user and/or said localized sound sources in said environment over time.

6. A hearing system according to claim 1 wherein the audio input unit comprises a microphone array comprising a multitude of microphones for picking up sound from said environment and providing respective microphone signals comprising sound from said number of localized sound sources and providing at least some of said multitude of audio signals.

7. A hearing system according to claim 6 comprising a head worn frame or structure whereon at least some of said multitude of microphones are located.

8. A hearing system according to claim 1 comprising one or two hearing devices configured to be located at or in respective left and right ears of a user, and a head worn frame or structure, wherein or whereon one or more of said sensors are mounted.

9. A hearing system according to claim 8 wherein communication between the one or two hearing devices and the one or more sensors, is wired or wireless.

10. A hearing system according to claim 1 wherein said sensor unit comprises one or more of an accelerometer, a gyroscope, and a magnetometer.

11. A hearing system according to claim 1 wherein said sensor unit comprises one or more of said sensors, and wherein at least one of said one or more sensors comprises an electrode for picking up body signals.

12. A hearing system according to claim 1 wherein said sensor unit comprises one or more vision sensors.

13. A hearing system according to claim 1 wherein said first processor comprises a simultaneous localization and mapping (SLAM) algorithm.

14. A hearing system according to claim 1 wherein said first processor comprises a face recognition algorithm for identifying one or more faces in the environment of the user.

15. A hearing system according to claim 1 wherein the hearing device comprises a hearing aid, a headset, an earphone, an ear protection device or a combination thereof.

16. A method of operating a hearing system comprising a hearing device, the hearing device being adapted for being worn by a user, the method comprising
receiving and/or providing audio signals comprising sound from a number of localized sound sources in an environment around the user,
receiving sensor signals from one or more sensors, said one or more sensors being located in said environment and/or form part of said hearing system,
generating and updating over time data representative of a map of said environment of the user, said data being termed map data, said environment comprising a number of, stationary or mobile, landmarks, said landmarks comprising said number of localized sound sources, and said map data being representative of the physical location of said landmarks in the environment relative to the user;
generating and updating over time said map data based on said audio signals and said sensor signals;
providing one or more beamformers based on said audio signals,
controlling and updating over time the one or more beamformers in dependence of the map data, and to direct the one or more beamformers towards one or more of the localized sound sources in the environment of the user,
enhancing said multitude of audio signals and providing a processed electric output signal comprising one or more of the localized sound sources based on the one or more beamformers, and
providing stimuli perceivable as sound to the user based on said processed electric output signal representing or comprising sound from said one or more of said localized sound sources by an output unit of said hearing device.

17. A hearing system according to claim 1 wherein said localized sound sources are constituted by or comprises a speech source originating from a person talking or from a localized sound transducer.

18. A hearing system according to claim 1 wherein number of localized sound sources is larger than or equal to two.

19. A hearing system according to claim 1 wherein localized sound sources are stationary or mobile.

* * * * *